(12) United States Patent
Purschke et al.

(10) Patent No.: US 8,383,789 B2
(45) Date of Patent: Feb. 26, 2013

(54) VASOPRESSIN-BINDING L-NUCLEIC ACID

(75) Inventors: Werner Purschke, Berlin (DE); Dirk Eulberg, Berlin (DE); Sven Klussmann, Berlin (DE); Ingo Rohl, Berlin (DE); Axel Vater, Berlin (DE)

(73) Assignee: NOXXON Pharma AG, Berlin (DE)

( * ) Notice: Subject to any disclaimer, the term of this patent is extended or adjusted under 35 U.S.C. 154(b) by 770 days.

(21) Appl. No.: 11/791,891

(22) PCT Filed: Nov. 29, 2005

(86) PCT No.: PCT/EP2005/012744
§ 371 (c)(1),
(2), (4) Date: May 29, 2007

(87) PCT Pub. No.: WO2006/058705
PCT Pub. Date: Jun. 8, 2006

(65) Prior Publication Data
US 2009/0181909 A1 Jul. 16, 2009

(30) Foreign Application Priority Data
Nov. 29, 2004 (DE) .................. 10 2004 057 523

(51) Int. Cl.
*C07H 21/02* (2006.01)
*C07H 21/04* (2006.01)
*A61K 48/00* (2006.01)

(52) U.S. Cl. ............. 536/23.1; 536/24.5; 514/44 R

(58) Field of Classification Search ............... 536/23.1, 536/24.5; 514/44 R; 435/6
See application file for complete search history.

(56) References Cited

U.S. PATENT DOCUMENTS

| | | |
|---|---|---|
| 5,668,264 A | 9/1997 | Janjic |
| 5,674,685 A | 10/1997 | Janjic |
| 5,723,594 A | 3/1998 | Janjic |
| 6,229,002 B1 | 5/2001 | Janjic |
| 6,329,145 B1 | 12/2001 | Janjic |
| 6,582,918 B2 | 6/2003 | Janjic |
| 6,670,132 B2 | 12/2003 | Janjic |
| 6,699,843 B2 | 3/2004 | Pietras |
| 7,258,980 B2 | 8/2007 | Janjic |
| 7,629,456 B2 | 12/2009 | Lange |
| 7,750,140 B2 | 7/2010 | Helmling et al. |
| 2010/0081710 A1 | 4/2010 | Lange |

FOREIGN PATENT DOCUMENTS

| | | | |
|---|---|---|---|
| WO | WO 95/07364 | * | 3/1995 |
| WO | WO98/34879 | | 11/1996 |
| WO | WO9634879 | | 11/1996 |
| WO | WO2004/13274 | | 2/2004 |

OTHER PUBLICATIONS

Nolte et al., Mirror-design of L-oligonucleotide ligands binding to L-arginine.Nat Biotechnol. Sep. 1996;14(9):1116-9.*
Klussmann et al Mirror-image RNA that binds D-adenosine. Nat Biotechnol. Sep. 1996;14(9):1112-5.*
Famulok et al., 2000, Nucleic Acid Aptamers From Selection in Vitro to Applications in Vivo Acc. Chem. Res. pp. 591-599.*
Williams et al. Bioactive and nuclease-resistant L-DNA ligand ofvasopressinPNAS 1997, pp. 11285-11290.*
Mishra et al., PEGylation significantly affects cellular uptake and intracellular trafficking of non-viral gene delivery particles European Journal of Cell Biology vol. 83, Issue 3, 2004, pp. 97-111.*
Eulberg et al., "Spiegelmers: Biostable Aptamers," ChemBioChem, 2003, 4, Wiley-VCH Verlag GmbH & Co., pp. 979-983.
Michaud et al., "A DNA Aptamer As a New Target-Specific Chiral Selector for HPLC," J. Am. Chem. Soc., 2003, 125, pp. 8672-8679.
Williams et al., "Bioactive and Nuclease-Resistant L-DNA Ligand of Vasopressin," Proc. Natl. Acad. Sci. USA, vol. 94, Oct. 1997, pp. 11285-11290.
Eulberg et al., "Spiegelmers: Biostable Aptamers," ChemBioChem 4:979-983, 2003.
Michaud et al., "A DNA Aptamer . . . HPLC," J Am Chem Soc 125:8672-8679, 2003.
Eulberg & Klussmann, "Spiegelmers: Biostable Aptamers," ChemBioChem 4:979-983, 2003.
Michaud et al., "A DNA . . . for HPLC," J Am Chem Soc 125:8672-8679, 2003.
Williams et al., "Bioactive . . . vasopressin," PNAS 94:11285-11290, 1997.

* cited by examiner

*Primary Examiner* — Maria Leavitt
(74) *Attorney, Agent, or Firm* — MDIP LLC

(57) ABSTRACT

The present invention relates to a vasopressin-binding nucleic acid, characterized in that the nucleic acid contains a stretch Box1 and a stretch Box2,
in which Box1 comprises the sequence GUGGW and W=A or U, preferably W=U, and
in which Box2 comprises a sequence of about 18 to 24 nucleotides, preferably 21 nucleotides, and a group $(G)_n$ is contained four times in the sequence, in which n=2, 3 or 4.

18 Claims, 18 Drawing Sheets

Fig. 1 Schematic diagram of automated RNA-selection
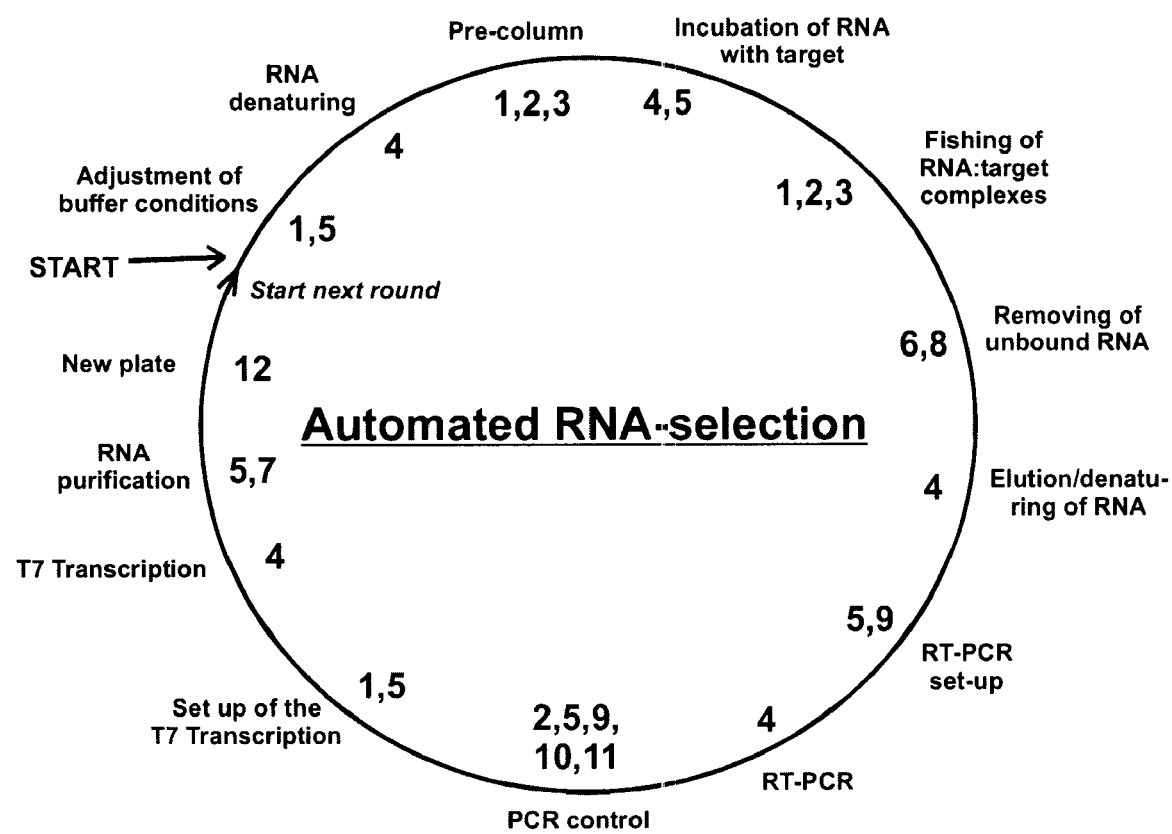

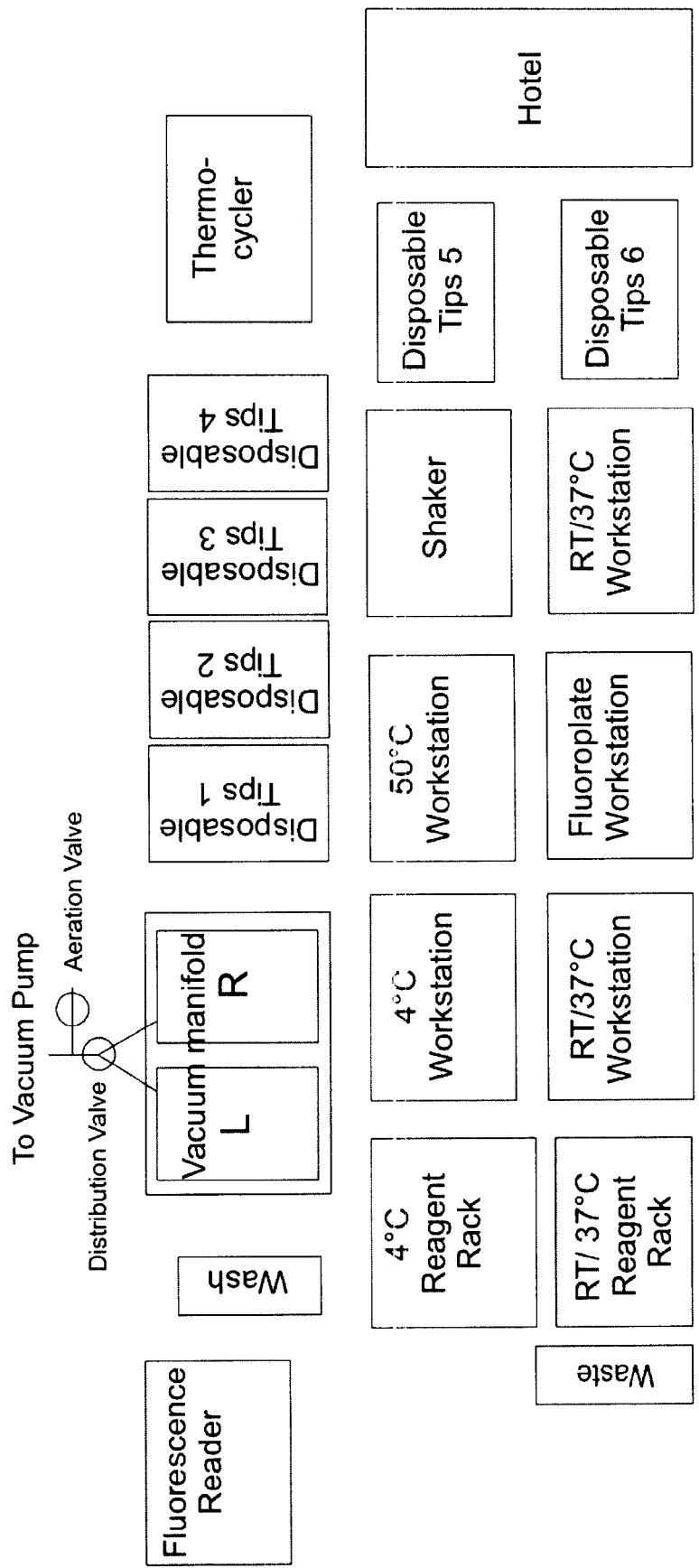
Fig. 2 Schematic diagram of robot's workspace for *in vitro* selection

Fig. 3 AVP-binding clones subsequent to the automated in vitro selection

Selected clones subsequent to the automated selection

| Clone | Sequence | [nt] | properties |
|---|---|---|---|
| CHF-134-B10 | AGCGUGC GUGGU UA--GUA-AU GGGGUAGGGAUUGGAUG-GGAA GCACGCU | 47 | second best binder |
| CHF-134-A9  | AGCGUGC GUGGA AA--UUAUAU GGGGUAGGGCUUGGAAG-GGUA GUACGCU | 48 | best binder |
| CHF-134-A10 | AGCGUGC GUGGA UA--GUA-AU GGGGUAGGGAUUGGAUG-GGUA GCACGCU | 47 | binds |
| CHF-134-H10 | AGCGUGC GUGGA AA--UUAUAUGGGGUAGGGCUUGGAAG-GGUA GUACGCU | 49 | binds |
| CHF-134-D12 | AGCGUGC GUGGA UA--AUA-AU GGGGUAGGGAUUGGAUG-GGUA GCACGCU | 47 | binds |
| CHF-134-E10 | AGCGUGC GUGGU UA--GUA-AU GGGGUAGGGAUUGGAAG-GGUA GCACGCU | 47 | binds |
| CHF-134-E11 | AGCGUGC GUGGU UA--GUA-AU GGGGUAGGGAUUGGAUG-GGUA GCACGCU | 47 | binds |
| CHF-134-B12 | AGCGUGC GUGGU AA--AUA-AU GGGGUAGGGAUUGGAUG-GGAA GCACGCU | 47 | binds |
| CHF-134-B11 | AGCGUGC GUGGU UA--GUA-AU GGGGUAGGGAUUGGAUG-GGUA GCACGCU | 47 | binds |
| CHF-134-A11 | AGCGUGC GUGGU AUUUGUA-AU GGGGUAGGGAUUGGAUG-GGUA GCACGCU | 49 | binds |
| CHF-134-E8  | AGCGUGC GUGGA UA--GUA-AU GGGGUAGGGAUUGGAUGUGGUA GUACGCU | 48 | binds |
| CHF-134-G5  | AGCGUGC GUGGA UA--GUA-AU GGGGUAGGGAUUGGAUG-GGUA GCACGCU | 47 | binds |
| CHF-134-F5  | AGCGUGC GUGGU UA--GUA-AU GGGGUAGGGAUUGGAUGUGGAA GCACGCU | 48 | binds |
| CHF-134-C8  | AGCGUGC GUGGA AA--UUAUAU GGGGUAGGGCUUGGAAG-GGAA GUACGCU | 48 | binds |
| CHF-134-A8  | AGCGUGC GUGGU AA--AUAAUA GGGGUAGGAUUGGAUG-GGAA GUACGCU | 48 | binds |

AVP-binding consensus-sequence consensus 5'-|Helix1|-|Box1|-WW---DWW--WW-|Box2|-|Helix2|-3' 47-49

```
         7nt    GUGGW   7-9nt    GGGGUAGGGMUUGGAWG-GGWA    7nt
```

Helix-region

Fig. 4 AVP-binding clones and consensus sequence subsequent to the in vitro selection

Selected clones subsequent to the automated selection

| Clone | Sequence | | | | | | [nt] | properties |
|---|---|---|---|---|---|---|---|---|
| CHF-134-B10 | AGCGUGC | GUGGU | UAGU--AAU | GGGUAGGGAUUGGAUGGGAA | GCACGCU | | 47 | second best binder subseq. to autom. sel. |
| CHF-134-A9 | AGCGUGC | GUGGA | AA-UUAUAU | GGGUAGGGCUUGGAAGGGUA | GUACGCU | | 48 | best binder subseq. to autom. sel. |

Clones subsequent to manual, mutagenic high-stringent selection

| Clone | | | | | | | [nt] | properties |
|---|---|---|---|---|---|---|---|---|
| CHF-157-A2 | AGUACGC | GUGGU | AAAUUGAAU | GGGUAGGGCUUGGACGGGUA | GUGUACU | | 49 | binds |
| CHF-157-H3 | AGGACGC | GUGGU | AA-UUAUAU | GGGUAGGCCUUGGAUGGGUA | GUGUCCU | | 48 | binds |
| CHF-157-C4 | AGUAUGC | GUGGU | AAAUUAAAU | GGGUAGGGCUUGGACGGGUA | GUGUACU | | 49 | binds |
| CHF-157-A4 | AGUAUGC | GUGGU | AAAUGAU-U | GGGUAGGGCUUGGAUGGGUA | GUGUACU | | 48 | binds |
| CHF-157-G3 | AGUAUGC | GUGGU | AAAUGAU-U | GGGUAGGGCUUGGAAUUGGUA | GUGUACU | | 48 | binds |
| CHF-157-H1 | AGUAUGC | GUGGU | AUAU--AAU | GGGUAGGGCUUGGAUGGGUA | GUGUACU | | 47 | binds |
| CHF-157-B2 | AGUACGC | GUGGU | U--UAAAAU | GGGUAGGGAUUGGAUGGGUA | GUGUACU | | 47 | binds |
| CHF-157-C1, C2 | AGUCUGC | GUGGU | UUUUU-AAU | GGGUAGGGCUUGGAUGGGUA | GUAGACU | | 48 | binds |
| CHF-157-E1 | AGUCUGC | GUGGU | UUUUU-AU | GGGUAGGGCUUGGAUGGGUA | GUAGACU | | 48 | binds |
| CHF-157-C3 | AGUCUGC | GUGGU | UUUUAAAUU | GGGUAGGGCUUGGAUGGGUA | GUAGACU | | 49 | binds |
| CHF-157-B3 | AGUAUGC | GUGGU | UUUU---AAU | GGGUAGGGCUUGGAUGGGUA | GUAUACU | | 47 | binds |
| CHF-157-A3 | AGUGUGC | GUGGU | UAG---AAU | GGGUAGGGCUUGGAUGGGUA | GUACACU | | 46 | binds |
| CHF-157-B4 | AGUGUGC | GUGGU | UAAU--AAU | GGGUAGGGCUUGGAUGGGUA | GUACACU | | 47 | sec. best binder subseq. to man. mut. sel. |
| CHF-157-E2, E3 | AGUGUGG | GUGGU | UAAU--AAU | GGGUAGGGCUUGGAUGGGUA | CCACACU | | 47 | best binder subseq. to man. mut. sel.* |
| CHF-157-D2 | AGUAUGG | GUGGU | UAUU--AAU | GGGUAGGGAUUGGAUGGGUA | CCAUACU | | 47 | binds |
| CHF-157-D1 | AGUAACC | GUGGU | UUA---AAU | GGGUAGGGAUUGGAUGGGCA | GGAUACU | | 46 | binds |
| CHF-157-G2 | AGUAGCC | GUGGU | UUA---AAU | GGGUAGGGAUUGGAUGGGCA | GGAUACU | | 46 | binds |
| CHF-157-D3 | AGUAGCC | GUGGU | AAAU--AAU | GGGUAGGGAUUGGAUGGGCA | GGACACU | | 47 | binds |
| CHF-157-F3 | AGUGACC | GUGGU | AAAU--GAU | GGGUAGGGAUUGGAUGGGCU | GGACACU | | 47 | binds |
| CHF-157-F1, G1 | AGUGACC | GUGGU | AAAU--AUU | GGGUAGGGAUUGGAUGGGCA | GGACACU | | 47 | binds |
| CHF-157-D4 | AGUAUGC | GUGGU | AAAU--AGU | GGGUAGGGAUUGGAUGGGCA | GUAUACU | | 47 | binds |

AVP-binding consensus sequence

Konsensus 5'- |Helix1|-|Box1|-WWDWDDWWU |  Box2  |-|Helix2|-3' 46-49
          7nt        GUGGW   6-9nt        GGGUAGGGMUUGGAHGGGHA        7nt Helix-region CHF-157-B4 binds approx. 12-fold better than CHF-134-A9

Fig. 5  Comparison of the best clones identified by automated selection and manual high-stringent selection
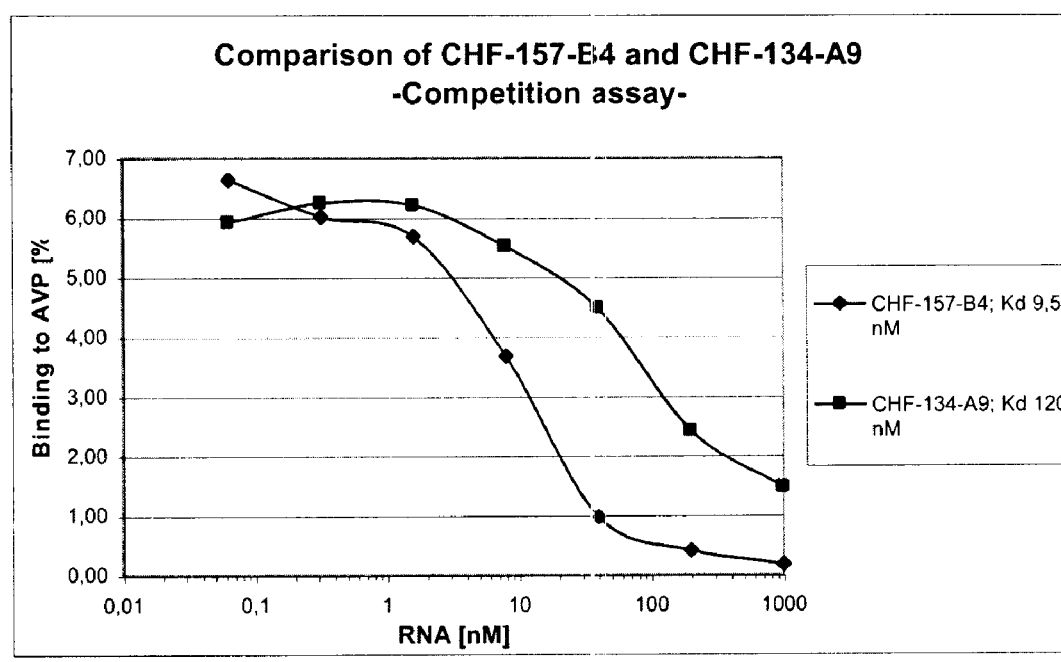

Fig. 6 Variants of sequences as result of site-directed modification and truncation using internal PEG-spacer moieties

A: Variants with unaltered 5'- and 3'-end

Best clone after the selection process

| | | | | | | | | [nt] | properties |
|---|---|---|---|---|---|---|---|---|---|
| CHF-F-000 | AGUGUGC | GUGGU | UAAUAAU | GGGGUAGGGCUUGGAUGGGUA | GUACACU | | | 47 | best binder after man. mut. sel. |

Variants with internal PEG-spacer and unaltered 5'- and 3'-end

| | | | | | | [nt] | properties |
|---|---|---|---|---|---|---|---|
| CHF-F-002 | AGUGUGC | GUGG | ---AUAAU | GGGGUAGGGCUUGGAUGGGUA | GUACACU | 44 | binds inferior CHF-F-000 |
| CHF-F-003 | AGUGUGC | GUGGU | ---UAAU | GGGGUAGGGCUUGGAUGGGUA | GUACACU | 44 | 2-fold better than CHF-F-000 |
| CHF-F-004 | AGUGUGC | GUGGU | U---AAU | GGGGUAGGGCUUGGAUGGGUA | GUACACU | 44 | binds |
| CHF-F-005 | AGUGUGC | GUGGU | UA--AU | GGGGUAGGGCUUGGAUGGGUA | GUACACU | 44 | binds |
| CHF-F-006 | AGUGUGC | GUGGU | UAA---U | GGGGUAGGGCUUGGAUGGGUA | GUACACU | 44 | binds |
| CHF-F-007 | AGUGUGC | GUGGU | UAAU--- | GGGGUAGGGCUUGGAUGGGUA | GUACACU | 44 | binds |
| CHF-F-008 | AGUGUGC | GUGGU | UAAUAAU | GGGGU---GCUUGGAUGGGUA | GUACACU | 44 | binds not |
| CHF-F-009 | AGUGUGC | GUGGU | UAAUAAU | GGGGUAGGGCUU---UGGGUA | GUACACU | 44 | binds not |
| CHF-F-010 | AGUGUGC | GUGGU | ------- | GGGGUAGGGCUUGGAUGGGUA | GUACACU | 41 | binds |
| CHF-F-011 | AGUGUGC | GUGGU | --- AAU | CCCUACCCUUGGAUGGGUA | GUACACU | 43 | 2-fold better than CHF-F-000 |
| CHF-F-019 | AGUGUGC | GUGGU | ------AU | GGGGUAGGGCUUGGAUGGGUA | GUACACU | 42 | binds |
| CHF-F-020 | AGUGUGC | GUGGU | ------U | GGGGUAGGGCUUGGAUGGGUA | GUACACU | 41 | binds |
| CHF-F-021 | AGUGUGC | GUGGU | ------- | GGGGUAGGGCUUGGAUGGGUA | GUACACU | 40 | binds |

AVP-binding consensus sequence of variants with internal PEG-spacer and unaltered 5'- and 3'-end Konsensus 5'- |Helix1|- |Box1| -WWWW- |Box2| -|Helix2| -3' 40-44
             7nt    GUGGU        GGGUAGGGM

Fig. 7 Variants of sequences as result of site-directed modification and truncation using internal PEG-spacer moieties

B: Variants with altered 5'- and 3'-end

Best variants with internal PEG-spacer and unaltered 5'- and 3'-end

| Name | 5' | Sequence | 3' | [nt] | properties |
|---|---|---|---|---|---|
| CHF-F-003 | AGUGUGC GUGGU ---UAAU | GGGUAGGGCUUGGAUGGGUA | GUACACU | 44 | 2-fold better than CHF-F-000 |
| CHF-F-011 | AGUGUGC GUGGU --- AAU | GGGUAGGGCUUGGAUGGGUA | GUACACU | 43 | 2-fold better than CHF-F-000 |

Variants with internal PEG-spacer and altered 5'- and 3'-end

| Name | 5' | Sequence | 3' | [nt] | properties |
|---|---|---|---|---|---|
| CHF-F-001 | AAUAAU GGGUAGGGCUUGGAUGGGUA GUACACU ---AGUGUGC GUGGU U | | | 47 | binds inferior CHF-F-018 |
| CHF-F-014 | UAAUAAU GGGUAGGGCUUGGAUGGGUA GUACACU ---AGUGUGC GUGGU | | | 47 | binds inferior CHF-F-018 |
| CHF-F-015 | UAAU GGGUAGGGCUUGGAUGGGUA GUACACU ---AGUGUGC GUGGU | | | 44 | binds inferior CHF-F-018 |
| CHF-F-016 | AAU GGGUAGGGCUUGGAUGGGUA GUACACU ---AGUGUGC GUGGU | | | 43 | binds inferior CHF-F-018 |
| CHF-F-017 | AU GGGUAGGGCUUGGAUGGGUA GUACACU ---AGUGUGC GUGGU | | | 42 | binds inferior CHF-F-018 |
| CHF-F-018 | U GGGUAGGGCUUGGAUGGGUA GUACACU ---AGUGUGC GUGGU | | | 41 | binds as CHF-F-003 and CHF-F-011 |
| CHF-F-032 | U GGGUAGGGCUUGGAUGGGUA GUACACU ---AGUGUGC GUGG | | | 40 | binds inferior CHF-F-018 |
| CHF-F-033 | GGGUAGGGCUUGGAUGGGUA GUACACU ---AGUGUGC GUGGU | | | 40 | binds better than CHF-F-018 |
| CHF-F-034 | GGGUAGGGCUUGGAUGGGUA GUACACU ---AGUGUGC GUGG | | | 39 | binds inferior CHF-F-018 |
| CHF-F-035 | U GGGUAGGGCUUGGAUGGGUA GUACAC --- GUGUGC GUGGU | | | 39 | binds better than CHF-F-018 |
| CHF-F-036 | U GGGUAGGGCUUGGAUGGGUA GUACAC --- GUGUGC GUGG | | | 38 | binds inferior CHF-F-018 |
| CHF-F-037 | GGGUAGGGCUUGGAUGGGUA GUACAC --- GUGUGC GUGGU | | | 38 | binds better than CHF-F-018 |
| CHF-F-038 | GGGUAGGGCUUGGAUGGGUA GUACAC --- GUGUGC GUGG | | | 37 | binds inferior CHF-F-018 |

Finale candidate

| CHF-F-037 | GGGUAGGGCUUGGAUGGGUA GUACAC --- GUGUGC GUGGU | 38 | binds best: Kd 1,5 nM (ITC) |
|---|---|---|---|

AVP-binding consensus sequence of variants with internal PEG-spacer and altered 5'- and 3'-end

Konsensus  5'- WWWWW- [Box2] ---- [Helix2] ---- [Helix1] -[Box1] -3'  38-47
            0-7nt   GGGUAGGGMUUGGAHGGGUA  6-7nt     6-7nt   GUGGU — Helix-region
--- PEG-Spacer

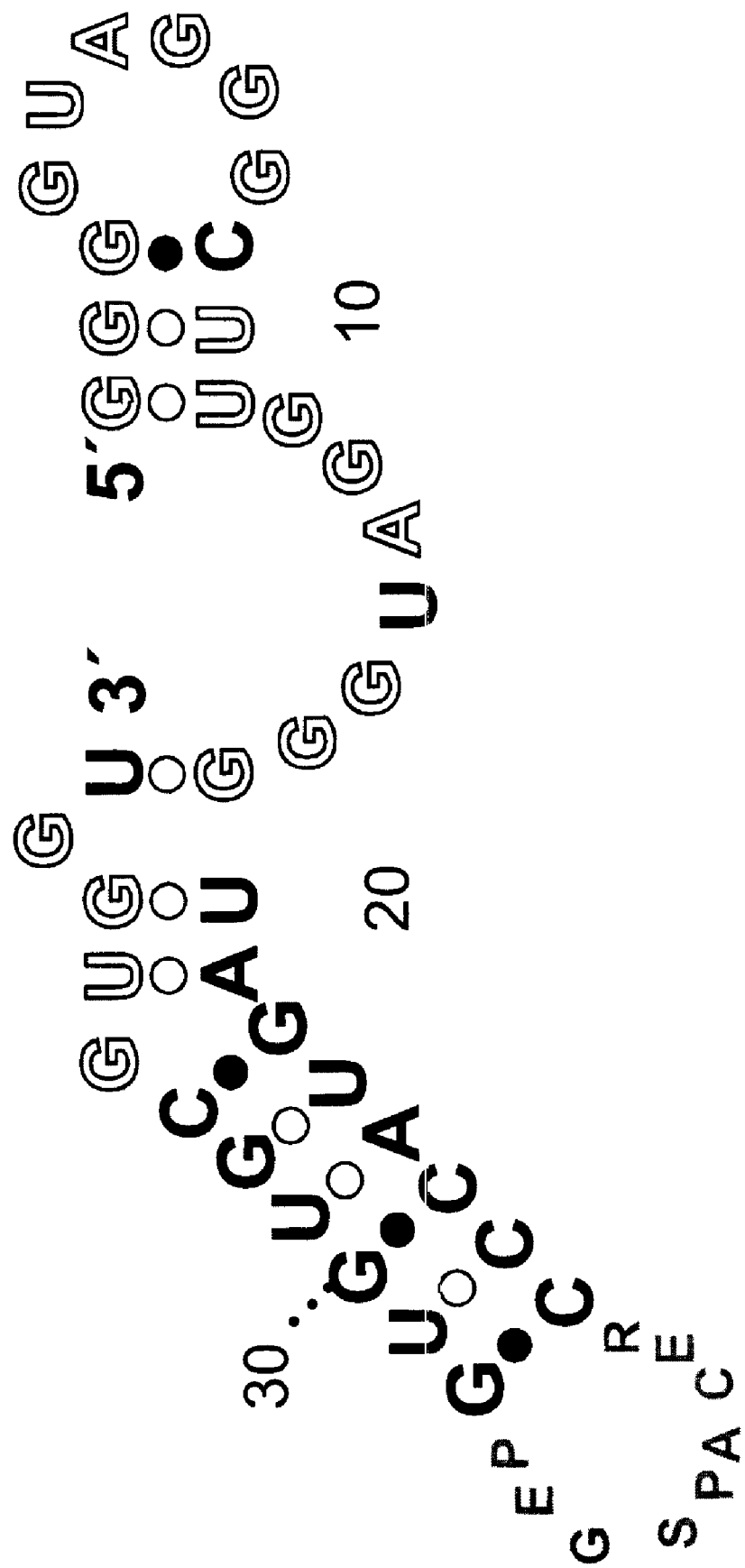
Fig. 8 Secondary structure model of AVP-binding Spiegelmer CHF-F-037

Fig. 9 Analytical IEX-HPLC of the 3'-amino-modified Spiegelmer CHF-F-037-3'NH$_2$
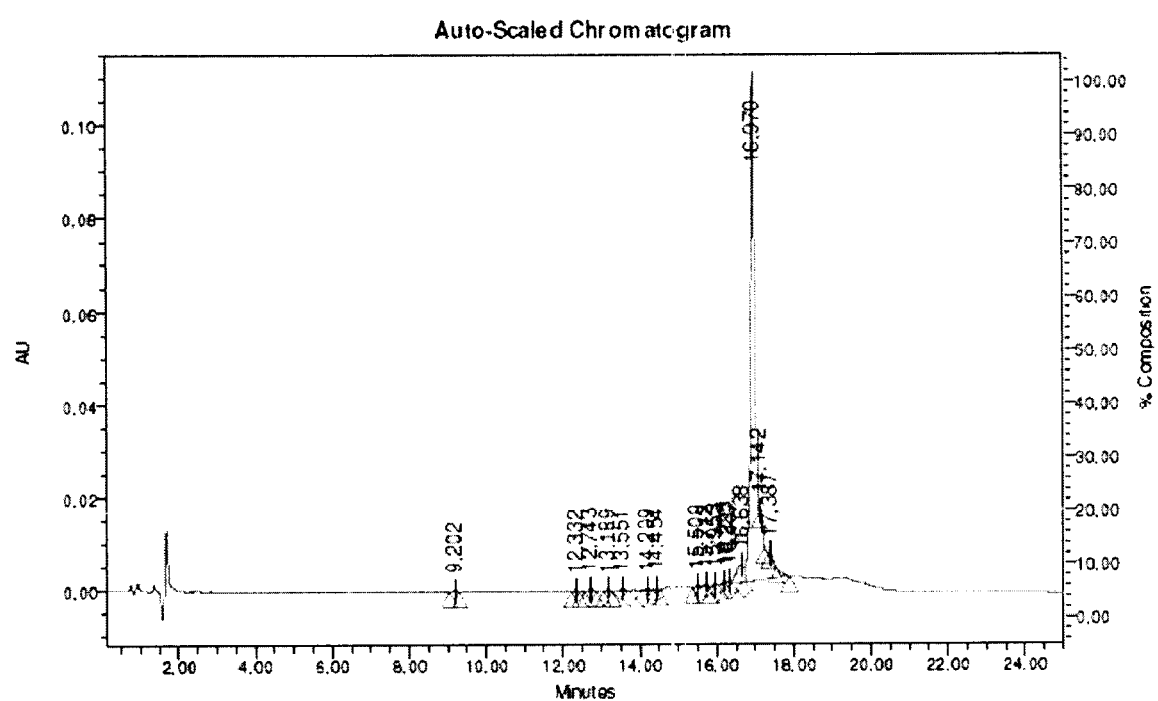

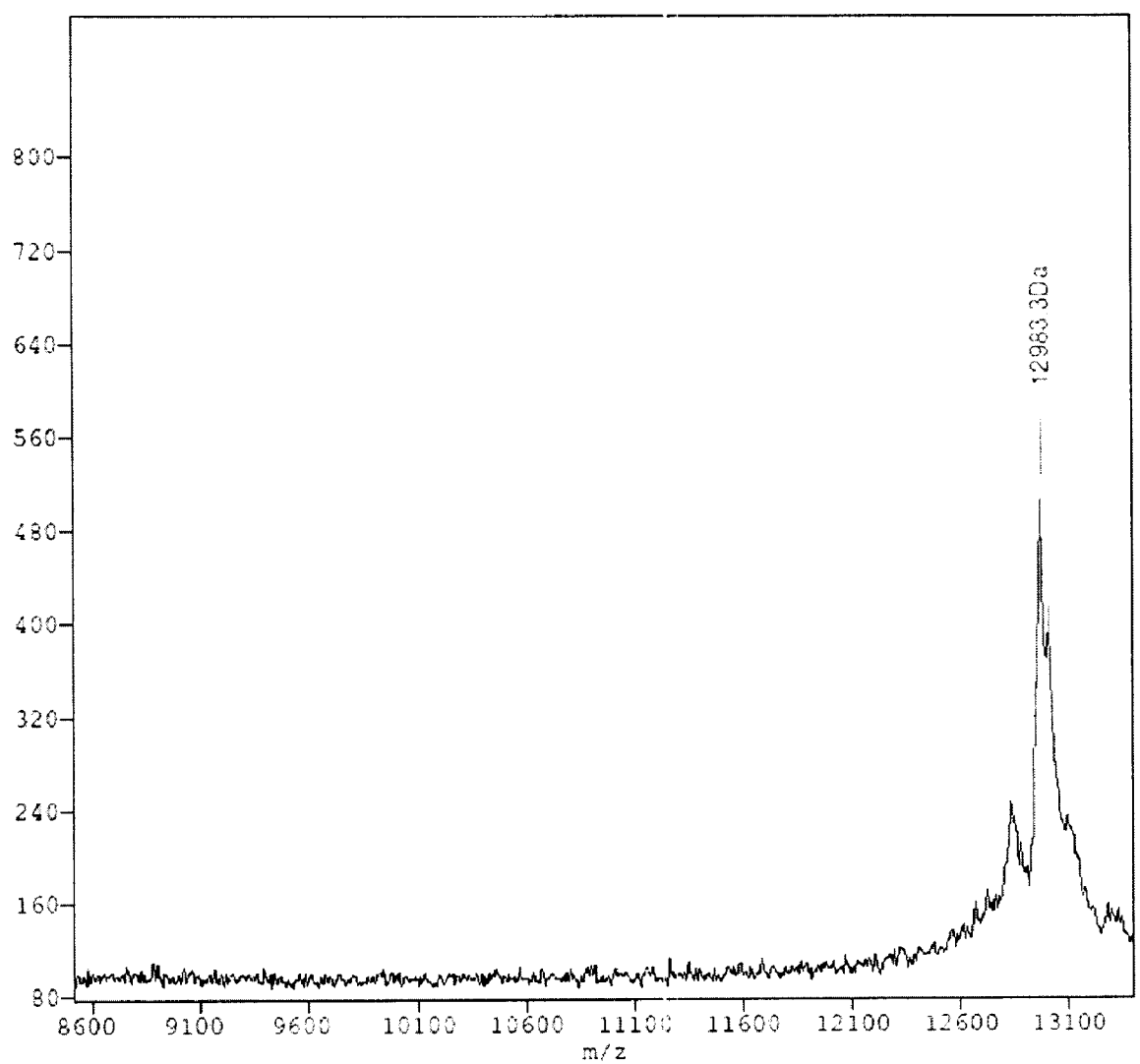
Fig. 10 MALDI-TOF of the 3'-amino-modified Spiegelmer CHF-F-037-3'NH$_2$ Fig. 11 CGE of the 3' -amino-modified Spiegelmer CHF-F-037-3'NH₂
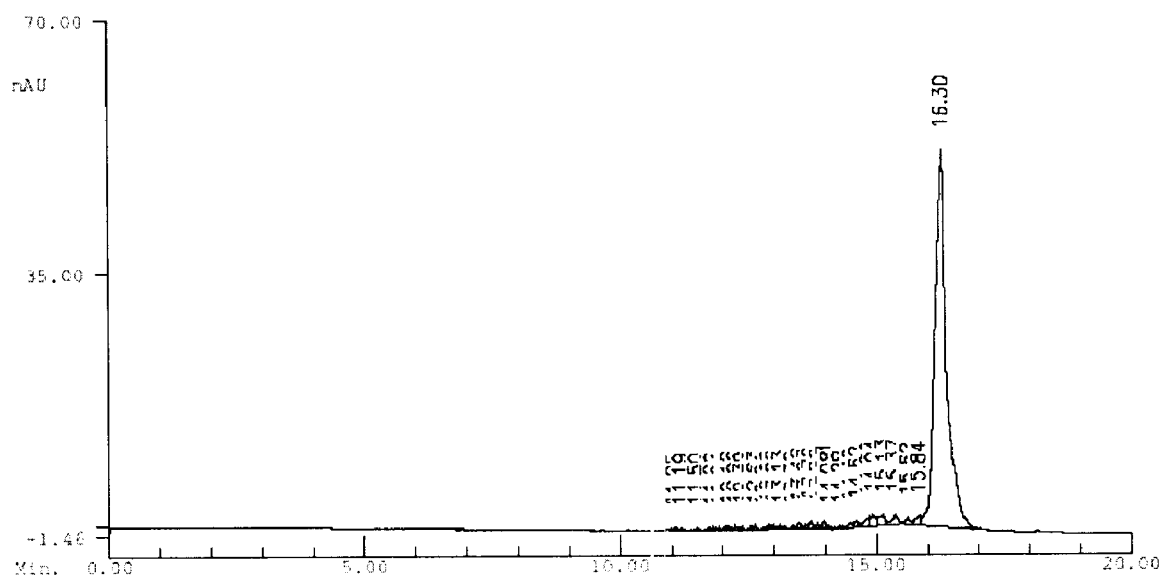

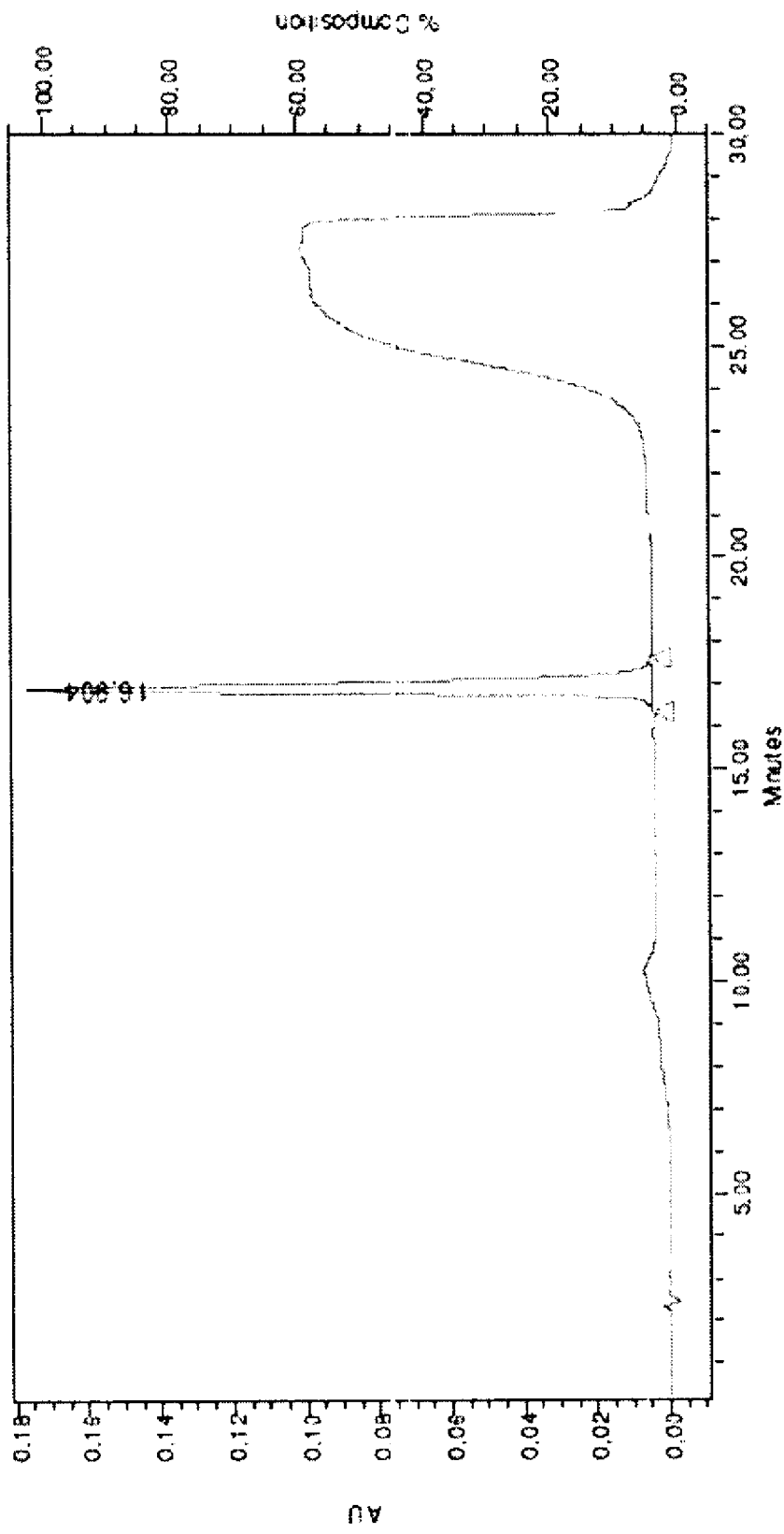
Fig. 12  Analytical RP-HPLC of 40kDa PEGylated Spiegelmer CHF-F-037-3'PEG. At 10 min retention time not converted 3'-amino-modified Spiegelmer is visible

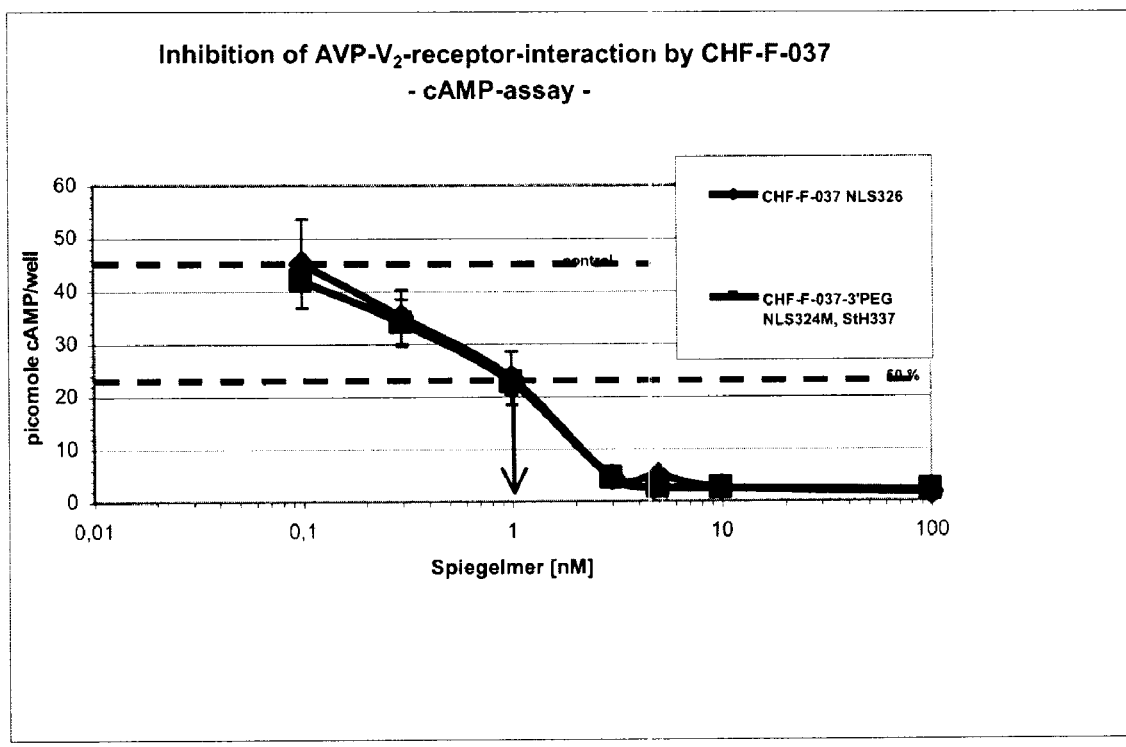
Fig. 13   Inhibition of AVP-V₂-receptor-interaction by CHF-F-037 und CHF-F-037-3'PEG

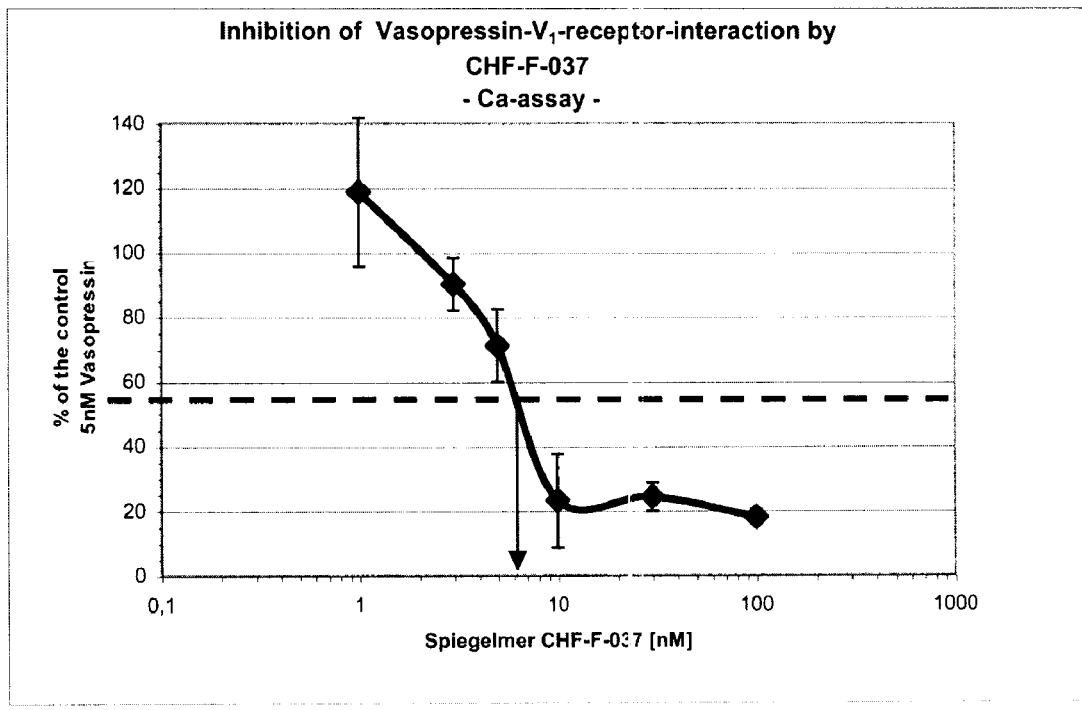
Fig. 14A
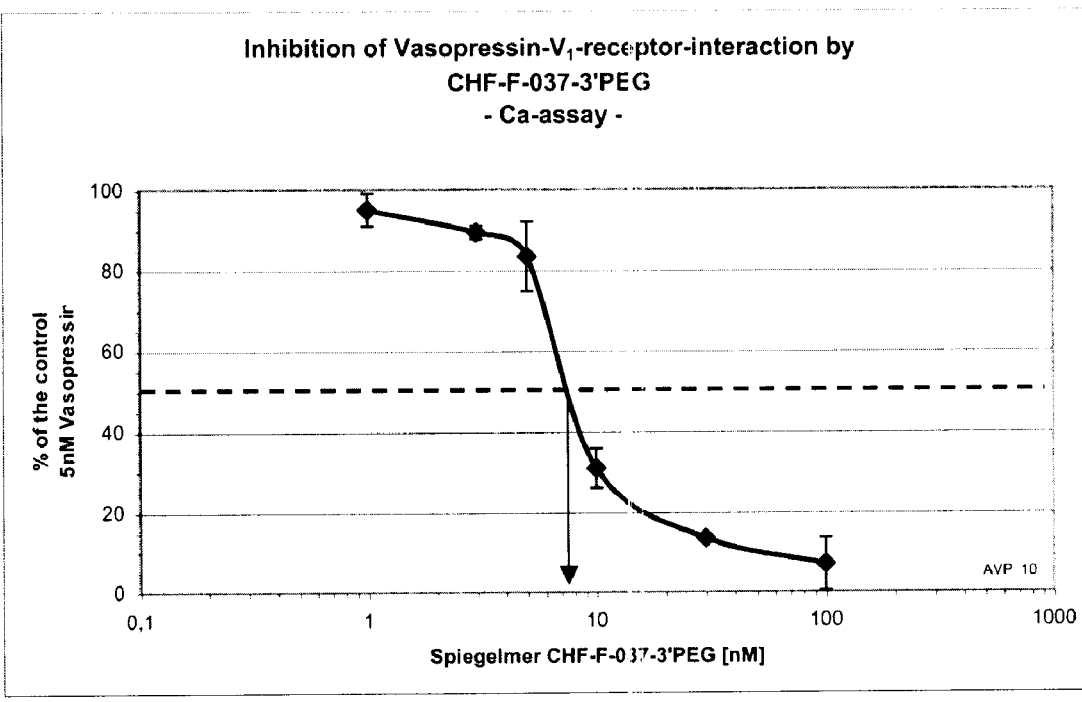
Fig. 14B  Inhibition of AVP-$V_1$-receptor-interaction by CHF-F-037 and CHF-F-037-3'PEG Fig. 15   Urine volume of the rats after Spiegelmer administration
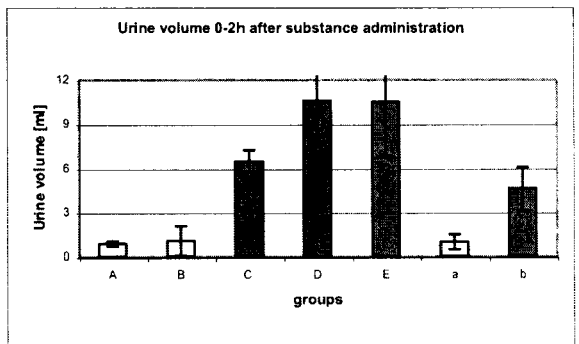
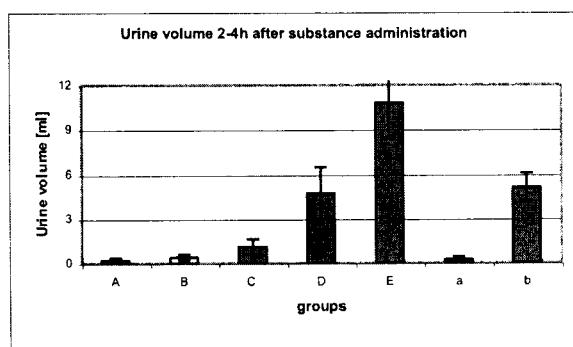
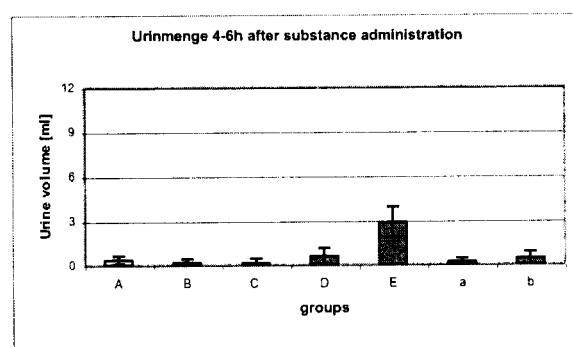
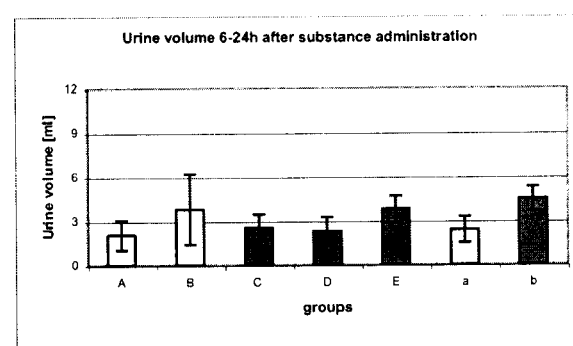
A: vehicle, i.v. (PBS, pH7)
B: control-PEG-Spiegelmer, i.v. (2000 nmol/kg)
C: active PEG-Spiegelmer, i.v. (80 nmol/kg)
D: active PEG-Spiegelmer, i.v. (400 nmol/kg)
E: active PEG-Spiegelmer, i.v. (2000 nmol/kg)
a: control-Spiegelmer, i.p. (2000 nmol/kg)
b: active-Spiegelmer, i.p. (2000 nmol/kg)

Fig. 17   Osmolality in the urine of the rats after Spiegelmer administration
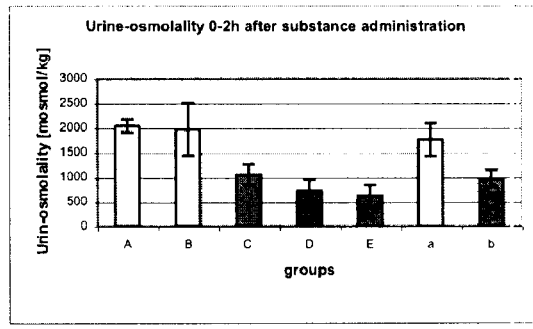
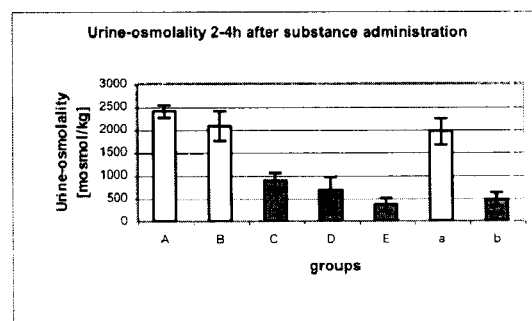
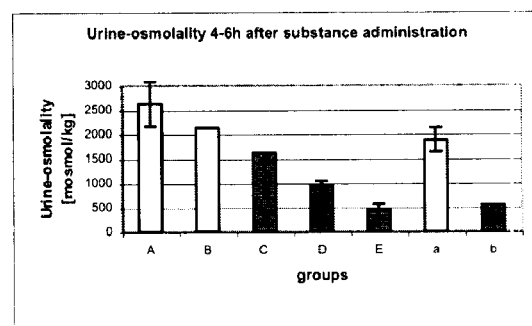
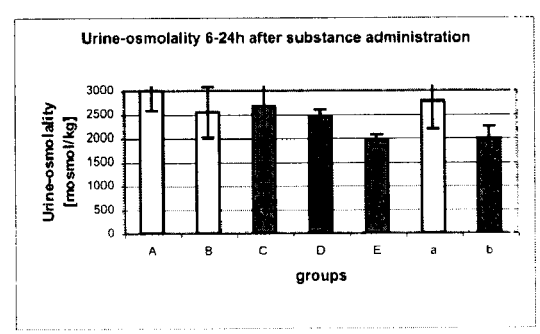
A: vehicle, i.v. (PBS, pH7)
B: control-PEG-Spiegelmer, i.v. (2000 nmol/kg)
C: active PEG-Spiegelmer, i.v. (80 nmol/kg)
D: active PEG-Spiegelmer, i.v. (400 nmol/kg)
E: active PEG-Spiegelmer, i.v. (2000 nmol/kg)
a: control-Spiegelmer, i.p. (2000 nmol/kg)
b: active-Spiegelmer, i.p. (2000 nmol/kg)

Fig. 18 Sodium content in the urine of the rats after Spiegelmer administration
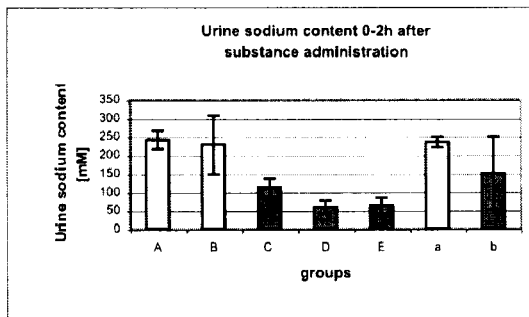
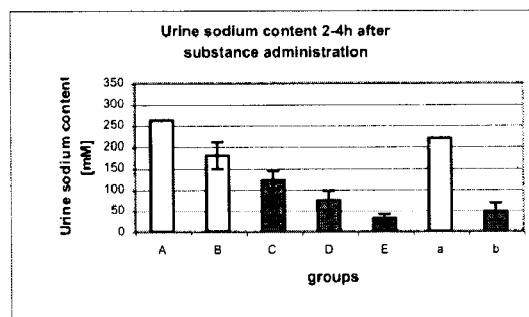
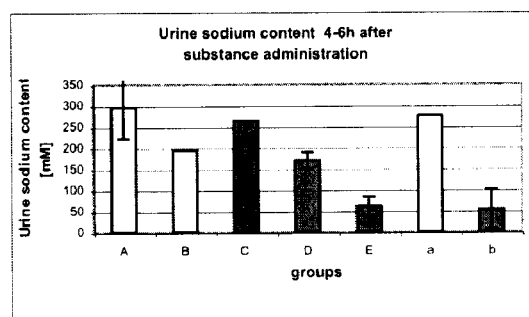
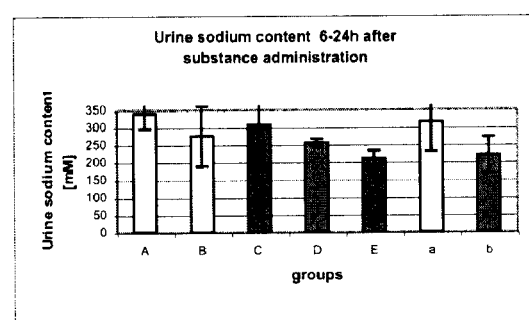
A: vehicle, i.v. (PBS, pH7)
B: control-PEG-Spiegelmer, i.v. (2000 nmol/kg)
C: active PEG-Spiegelmer, i.v. (80 nmol/kg)
D: active PEG-Spiegelmer, i.v. (400 nmol/kg)
E: active PEG-Spiegelmer, i.v. (2000 nmol/kg)
a: control-Spiegelmer, i.p. (2000 nmol/kg)
b: active-Spiegelmer, i.p. (2000 nmol/kg)

SEQUENCE LISTING

<160> NUMBER OF SEQ ID NOS: 93

<210> SEQ ID NO 1
<211> LENGTH: 9
<212> TYPE: PRT
<213> ORGANISM: Homo sapiens

<400> SEQUENCE: 1

Cys Tyr Phe Gln Asn Cys Pro Arg Gly
1               5

<210> SEQ ID NO 2
<211> LENGTH: 48
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
agcgugcgug gaaauuauau gggguagggc uuggaagggu aguacgcu                48

<210> SEQ ID NO 3
<211> LENGTH: 49
<212> TYPE: RNA
<213> ORGANISM: Artificial Sequence
<220> FEATURE:
<223> OTHER INFORMATION: Description of Artificial Sequence: Synthetic -continued oligonucleotide

<400> SEQUENCE: 3
aguacgcgug guaaauugaa ugggguaggg cuuggacggg uaguguacu        49

<210> SEQ ID NO 4
<211> LENGTH: 48
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4
aggacgcgug guaauuauau gggguagggc uuggaugggu aguguccu         48

<210> SEQ ID NO 5
<211> LENGTH: 49
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
aguaugcgug guaaauuaaa ugggguaggg cuuggacggg uaguguacu        49

<210> SEQ ID NO 6
<211> LENGTH: 48
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6
aguaugcgug guaaaugauu gggguagggc uuggaugggu aguguacu         48

<210> SEQ ID NO 7
<211> LENGTH: 48
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7
aguaugcgug guaaaugauu gggguagggc uugaauuggu aguguacu         48

<210> SEQ ID NO 8
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 8
aguaugcgug guauauaaug ggguagggcu uggaugggua guguacu          47

<210> SEQ ID NO 9
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide -continued

```
<400> SEQUENCE: 9
aguacgcgug guuuaaaaug ggguagggau uggaugggua gaguacu          47

<210> SEQ ID NO 10
<211> LENGTH: 48
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 10
agucugcgug guuuuuuaau gggguagggc uuggaugggu aguagacu         48

<210> SEQ ID NO 11
<211> LENGTH: 48
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 11
agucugcgug guuuuuuuau gggguagggc uuggaugggu aguagacu         48

<210> SEQ ID NO 12
<211> LENGTH: 49
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 12
agucugcgug guuuuuaaau uggguaggg cuuggauggg uaguagacu         49

<210> SEQ ID NO 13
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 13
aguaugcgug guuuuuaaug ggguagggcu uggaugggua guauacu          47

<210> SEQ ID NO 14
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 14
agugugcgug guuagaaugg gguagggcuu ggaugggu ag uacacu          46

<210> SEQ ID NO 15
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 15
```

-continued agugugcgug guuaauaaug ggguagggcu uggaugggua guacacu         47

<210> SEQ ID NO 16
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 16
agugugggug guuaauaaug gguagggcu uggaugggua ccacacu          47

<210> SEQ ID NO 17
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 17
aguaugggug guuauuaaug gguagggau uggaugggua ccauacu          47

<210> SEQ ID NO 18
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 18
aguaaccgug guuuaaaugg gguagggauu ggaugggcag gauacu          46

<210> SEQ ID NO 19
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 19
aguagccgug guuuaaaugg gguagggauu ggaugggcag gauacu          46

<210> SEQ ID NO 20
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 20
agugaccgug guaaauaaug gguagggau uggaugggca ggacacu          47

<210> SEQ ID NO 21
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 21
agugaccgug guaaaugaug gguagggau uggaugggcu ggacacu          47

-continued

<210> SEQ ID NO 22
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 22
agugaccgug guaaauauug ggguagggau uggaugggca ggacacu                47

<210> SEQ ID NO 23
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 23
aguaugcgug guaaauagug ggguagggau uggaugggca guauacu                47

<210> SEQ ID NO 24
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 24
agugugcgug guuaauaaug ggguagggcu uggaugggua guacacu                47

<210> SEQ ID NO 25
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 25
agugugcgug g                                                       11

<210> SEQ ID NO 26
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 26
agugugcgug gu                                                      12

<210> SEQ ID NO 27
<211> LENGTH: 13
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 27
agugugcgug guu                                                     13

<210> SEQ ID NO 28

```
<211> LENGTH: 14
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 28
agugugcgug guua                                                       14

<210> SEQ ID NO 29
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 29
agugugcgug guuaa                                                      15

<210> SEQ ID NO 30
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 30
agugugcgug guuaau                                                     16

<210> SEQ ID NO 31
<211> LENGTH: 29
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 31
ugggguaggg cuuggauggg uaguacacu                                       29

<210> SEQ ID NO 32
<211> LENGTH: 31
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 32 aauggguag ggcuuggaug gguaguacac u                                     31

<210> SEQ ID NO 33
<211> LENGTH: 30
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 33
augggguagg gcuuggaugg guaguacacu                                      30

<210> SEQ ID NO 34
<211> LENGTH: 29
<212> TYPE: RNA
```

<213> ORGANISM: Artificial Sequence
<220> FEATURE:
<223> OTHER INFORMATION: Description of Artificial Sequence: Synthetic
      oligonucleotide

<400> SEQUENCE: 34
ugggguaggg cuuggaugggu aguacacu                                    29

<210> SEQ ID NO 35
<211> LENGTH: 28
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 35
gggguagggc uuggaugggu aguacacu                                     28

<210> SEQ ID NO 36
<211> LENGTH: 32
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 36
uaauggggua gggcuuggau ggguaguaca cu                                32

<210> SEQ ID NO 37
<211> LENGTH: 31
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 37 aauggggguag ggcuuggaug gguaguacac u                                31

<210> SEQ ID NO 38
<211> LENGTH: 34
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 38
aauaaugggg uagggcuugg auggguagua cacu                              34

<210> SEQ ID NO 39
<211> LENGTH: 35
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 39
uaauaauggg guagggcuug gaugguagu acacu                              35

<210> SEQ ID NO 40
<211> LENGTH: 32
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 40
uaauggggua gggcuuggau ggguaguaca cu                                    32

<210> SEQ ID NO 41
<211> LENGTH: 31
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 41
aauggggUag ggcuuggaug gguaguacac u                                     31

<210> SEQ ID NO 42
<211> LENGTH: 30
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 42 auggguagg gcuuggaugg guaguacacu                                        30

<210> SEQ ID NO 43
<211> LENGTH: 29
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 43 uggguaggg cuuggauggg uaguacacu                                         29

<210> SEQ ID NO 44
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 44
agugugcgug g                                                           11

<210> SEQ ID NO 45
<211> LENGTH: 28
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 45
gggguagggc uuggaugggu aguacacu                                         28

<210> SEQ ID NO 46
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 46
agugugcgug g                                                              11

<210> SEQ ID NO 47
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 47
gugugcgugg u                                                              11

<210> SEQ ID NO 48
<211> LENGTH: 10
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 48
gugugcgugg                                                                10

<210> SEQ ID NO 49
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 49
gggguagggc uuggaugggu aguacac                                             27

<210> SEQ ID NO 50
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 50
gggguagggm uuggahgggh a                                                   21

<210> SEQ ID NO 51
<211> LENGTH: 49
<212> TYPE: RNA
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: modified_base
<222> LOCATION: (1)..(7)
<223> OTHER INFORMATION: a, c, u, g, unknown or other
<220> FEATURE:
<221> NAME/KEY: misc_feature
<222> LOCATION: (13)..(21)
<223> OTHER INFORMATION: This region may encompass 6 to 9 nucleotides
<220> FEATURE:
<221> NAME/KEY: modified_base
<222> LOCATION: (43)..(49)
<223> OTHER INFORMATION: a, c, u, g, unknown or other
<220> FEATURE:
<223> OTHER INFORMATION: see specification as filed for detailed
      description of consensus sequence
```

```
<400> SEQUENCE: 51
nnnnnnngug gwwwdwddww wgggguaggg muuggahggg hannnnnnn                          49

<210> SEQ ID NO 52
<211> LENGTH: 13
<212> TYPE: RNA
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: modified_base
<222> LOCATION: (1)..(7)
<223> OTHER INFORMATION: a, c, u, g, unknown or other
<220> FEATURE:
<223> OTHER INFORMATION: see specification as filed for detailed
      description of consensus sequence

<400> SEQUENCE: 52
nnnnnnngug gww                                                                 13

<210> SEQ ID NO 53
<211> LENGTH: 31
<212> TYPE: RNA
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: modified_base
<222> LOCATION: (25)..(31)
<223> OTHER INFORMATION: a, c, u, g, unknown or other
<220> FEATURE:
<223> OTHER INFORMATION: see specification as filed for detailed
      description of consensus sequence

<400> SEQUENCE: 53 wwwggguag ggmuuggahg gghannnnnn n                                              31

<210> SEQ ID NO 54
<211> LENGTH: 35
<212> TYPE: RNA
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: misc_feature
<222> LOCATION: (1)..(7)
<223> OTHER INFORMATION: This region may encompass 0 to 7 nucleotides
<220> FEATURE:
<221> NAME/KEY: modified_base
<222> LOCATION: (29)..(35)
<223> OTHER INFORMATION: a, c, u, g, unknown or other
<220> FEATURE:
<221> NAME/KEY: misc_feature
<222> LOCATION: (29)..(35)
<223> OTHER INFORMATION: This region may encompass 6-7 nucleotides
<220> FEATURE:
<223> OTHER INFORMATION: see specification as filed for detailed
      description of consensus sequence

<400> SEQUENCE: 54 wwwwwwggg guagggmuug gahggghann nnnnn                                          35

<210> SEQ ID NO 55
<211> LENGTH: 12
<212> TYPE: RNA
<213> ORGANISM: Artificial Sequence
<220> FEATURE:
<223> OTHER INFORMATION: Description of Artificial Sequence: Synthetic
``` consensus sequence
<220> FEATURE:
<221> NAME/KEY: modified_base
<222> LOCATION: (1)..(7)
<223> OTHER INFORMATION: a, c, u, g, unknown or other
<220> FEATURE:
<221> NAME/KEY: misc_feature
<222> LOCATION: (1)..(7)
<223> OTHER INFORMATION: This region may encompass 6-7 nucleotides
<220> FEATURE:
<223> OTHER INFORMATION: see specification as filed for detailed
      description of consensus sequence

<400> SEQUENCE: 55
nnnnnnngug gw                                                         12

<210> SEQ ID NO 56
<211> LENGTH: 33
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 56 auaaugggu agggcuugga uggguaguac acu                                   33

<210> SEQ ID NO 57
<211> LENGTH: 32
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 57 uaaugggua gggcuuggau ggguaguaca cu                                    32

<210> SEQ ID NO 58
<211> LENGTH: 31
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 58
aaugggguag ggcuuggaug gguaguacac u                                    31

<210> SEQ ID NO 59
<211> LENGTH: 30
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 59
augggguagg gcuuggaugg guaguacacu                                      30

<210> SEQ ID NO 60
<211> LENGTH: 29
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 60
ugggguaggg cuuggauggg uaguacacu        29

<210> SEQ ID NO 61
<211> LENGTH: 28
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 61
gggguagggc uuggaugggu aguacacu        28

<210> SEQ ID NO 62
<211> LENGTH: 13
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 62
agugugcgug guu        13

<210> SEQ ID NO 63
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 63
agugugcgug gu        12

<210> SEQ ID NO 64
<211> LENGTH: 28
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 64
ugggguaggg cuuggauggg uaguacac        28

<210> SEQ ID NO 65
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (23)..(56)
<223> OTHER INFORMATION: a, c, t, g, unknown or other

<400> SEQUENCE: 65
gtggaaccga ctcacctgag cgnnnnnnnn nnnnnnnnnn nnnnnnnnnn nnnnnncgct        60
gctgttgtct aagctcc        77

<210> SEQ ID NO 66
<211> LENGTH: 38
<212> TYPE: DNA
<213> ORGANISM: Artificial Sequence
<220> FEATURE:
<223> OTHER INFORMATION: Description of Artificial Sequence: Synthetic

```
                                       primer

<400> SEQUENCE: 66
tctaatacga ctcactatag gagcttagac aacagcag                              38

<210> SEQ ID NO 67
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
gtggaaccga ctcacctgag                                                  20

<210> SEQ ID NO 68
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 68
gggguagggm uuggawgggw a                                                21

<210> SEQ ID NO 69
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 69
agcgugcgug guuaguaaug ggguaggat uggaugggaa gcacgcu                     47

<210> SEQ ID NO 70
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 70
agcgugcgug gauaguaaug ggguagggau uggaugggua gcacgcu                    47

<210> SEQ ID NO 71
<211> LENGTH: 49
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 71
agcgugcgug gaaauuauau gggguaggg cuuggaaggg uaguacgcu                   49

<210> SEQ ID NO 72
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide
```

-continued

<400> SEQUENCE: 72
agcgugcgug gauaauaaug ggguagggau uggaugggua gcacgcu        47

<210> SEQ ID NO 73
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 73
agcgugcgug gauaguaaug ggguagggau uggaagggua gcacgcu        47

<210> SEQ ID NO 74
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 74
agcgugcgug guuaguaaug ggguagggau uggauggua gcacgcu         47

<210> SEQ ID NO 75
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 75
agcgugcgug guaaauaaug ggguagggau uggaugggaa guacgcu         47

<210> SEQ ID NO 76
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 76
agcgugcgug guuaguaaug ggguagggau uggaugggua gcacgcu        47

<210> SEQ ID NO 77
<211> LENGTH: 49
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 77
agcgugcgug guauuuguaa ugggguaggg auuggauggg uagcacgcu        49

<210> SEQ ID NO 78
<211> LENGTH: 48
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 78
agcgugcgug gauaguaaug gggguagggau uggauguggu aguacgcu                48

<210> SEQ ID NO 79
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 79
agcgugcgug gauaguaaug ggguagggau uggaugggua gcacgcu                 47

<210> SEQ ID NO 80
<211> LENGTH: 48
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 80
agcgugcgug gauaguaaug ggguagggau uggaugugga agcacgcu                48

<210> SEQ ID NO 81
<211> LENGTH: 48
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 81
agcgugcgug gaaauuauau gggguagggc uuggaaggga aguacgcu                48

<210> SEQ ID NO 82
<211> LENGTH: 48
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 82
agcgugcgug guaaauaaua ggggauagga uuggauggga aguacgcu                48

<210> SEQ ID NO 83
<211> LENGTH: 52
<212> TYPE: RNA
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: modified_base
<222> LOCATION: (1)..(7)
<223> OTHER INFORMATION: a, c, u, g, unknown or other
<220> FEATURE:
<221> NAME/KEY: misc_feature
<222> LOCATION: (13)..(23)
<223> OTHER INFORMATION: This region may encompass 7-9 nucleotides
<220> FEATURE:
<221> NAME/KEY: modified_base
<222> LOCATION: (15)..(16)
<223> OTHER INFORMATION: u or not present
<220> FEATURE:
<221> NAME/KEY: modified_base
<222> LOCATION: (20)..(20)
<223> OTHER INFORMATION: w or not present
<220> FEATURE:
<221> NAME/KEY: modified_base

```
<222> LOCATION: (23)..(23)
<223> OTHER INFORMATION: g or not present
<220> FEATURE:
<221> NAME/KEY: modified_base
<222> LOCATION: (41)..(41)
<223> OTHER INFORMATION: u or not present
<220> FEATURE:
<221> NAME/KEY: modified_base
<222> LOCATION: (46)..(52)
<223> OTHER INFORMATION: a, c, u, g, unknown or other
<220> FEATURE:
<223> OTHER INFORMATION: see specification as filed for detailed
      description of consensus sequence

<400> SEQUENCE: 83
nnnnnnngug gwwwuudwww wwgggggguag ggmuuggawg uggwannnnn nn          52

<210> SEQ ID NO 84
<211> LENGTH: 49
<212> TYPE: RNA
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: modified_base
<222> LOCATION: (1)..(7)
<223> OTHER INFORMATION: a, c, u, g, unknown or other
<220> FEATURE:
<221> NAME/KEY: misc_feature
<222> LOCATION: (13)..(21)
<223> OTHER INFORMATION: This region may encompass 6-9 nucleotides
<220> FEATURE:
<221> NAME/KEY: modified_base
<222> LOCATION: (43)..(49)
<223> OTHER INFORMATION: a, c, u, g, unknown or other
<220> FEATURE:
<223> OTHER INFORMATION: see specification as filed for detailed
      description of consensus sequence

<400> SEQUENCE: 84
nnnnnnngug gwwwdwddww uggggguaggg muuggahggg hannnnnnn             49

<210> SEQ ID NO 85
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 85
agugugcgug guuaauaaug gggu                                         24

<210> SEQ ID NO 86
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 86
gcuuggaugg guaguacacu                                              20

<210> SEQ ID NO 87
<211> LENGTH: 31
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 87
agugugcgug guuaauaaug ggguagggcu u                                    31

<210> SEQ ID NO 88
<211> LENGTH: 13
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 88
uggguaguac acu                                                        13

<210> SEQ ID NO 89
<211> LENGTH: 12
<212> TYPE: RNA
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: modified_base
<222> LOCATION: (1)..(7)
<223> OTHER INFORMATION: a, c, u, g, unknown or other
<220> FEATURE:
<223> OTHER INFORMATION: see specification as filed for detailed
      description of consensus sequence

<400> SEQUENCE: 89
nnnnnnngug gu                                                         12

<210> SEQ ID NO 90
<211> LENGTH: 32
<212> TYPE: RNA
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: modified_base
<222> LOCATION: (26)..(32)
<223> OTHER INFORMATION: a, c, u, g, unknown or other
<220> FEATURE:
<223> OTHER INFORMATION: see specification as filed for detailed
      description of consensus sequence

<400> SEQUENCE: 90 wwwwgggua gggmuuggah ggguannnnn nn                                    32

<210> SEQ ID NO 91
<211> LENGTH: 35
<212> TYPE: RNA
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: modified_base
<222> LOCATION: (1)..(1)
<223> OTHER INFORMATION: u or not present
<220> FEATURE:
<221> NAME/KEY: misc_feature
<222> LOCATION: (1)..(7)
<223> OTHER INFORMATION: This region may encompass 0-7 nucleotides
<220> FEATURE:
<221> NAME/KEY: modified_base
<222> LOCATION: (29)..(35)
<223> OTHER INFORMATION: a, c, u, g, unknown or other
<220> FEATURE:
<221> NAME/KEY: misc_feature
```

```
<222> LOCATION: (29)..(35)
<223> OTHER INFORMATION: This region may encompass 6-7 nucleotides
<220> FEATURE:
<223> OTHER INFORMATION: see specification as filed for detailed
      description of consensus sequence

<400> SEQUENCE: 91 uwwwwwggg guagggmuug gahggguann nnnnn                              35

<210> SEQ ID NO 92
<211> LENGTH: 12
<212> TYPE: RNA
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: modified_base
<222> LOCATION: (1)..(7)
<223> OTHER INFORMATION: a, c, u, g, unknown or other
<220> FEATURE:
<221> NAME/KEY: misc_feature
<222> LOCATION: (1)..(7)
<223> OTHER INFORMATION: This region may encompass 6-7 nucleotides
<220> FEATURE:
<223> OTHER INFORMATION: see specification as filed for detailed
      description of consensus sequence

<400> SEQUENCE: 92
nnnnnnngug gu                                                      12

<210> SEQ ID NO 93
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 93
gggguagggc uuggaugggu aguaccc                                      27
```

VASOPRESSIN-BINDING L-NUCLEIC ACID

SEQUENCE LISTING

The instant application contains a Sequence Listing which has been submitted in ASCII format via EFS-Web and is hereby incorporated by reference in its entirety. Said ASCII copy, created on Dec. 27, 2011, is named 21315855.txt and is 25,819 bytes in size.

The present invention relates to nucleic acids, their use for the production of a medicament as well as a diagnostic agent, complexes formed from the nucleic acid and vasopressin, as well as methods for screening vasopressin antagonists and vasopressin agonists.

Human vasopressin, also known as (arginine[8])-vasopressin (AVP) or as antidiuretic hormone (ADH), and also oxytocin are cyclic, nine amino acid long peptide hormones. These are neuropeptides, which are processed from precursor proteins after synthesis in the hypothalamus. Bound to a 10 kDa carrier protein which is processed from the same precursor protein from which the corresponding hormone originates, they pass via intracellular transport into the posterior lobe of the hypophysis, where they are stored, and after appropriate stimulation are secreted into the bloodstream. AVP has, starting from the amino end, the sequence: Cys-Tyr-Phe-Gln-Asn-Cys-Pro-Arg-Gly-$NH_2$ (SEQ. ID. NO. 1) with a molecular weight of 1085 Da. Oxytocin differs in its sequence from AVP only at position 3 (Ile) and at position 8 (Lys), and has a molecular weight of 1007 Da. Apart from the hypothalamus and hypophysis, AVP and oxytocin are also localised in neurons in other regions of the brain. Their role as neurotransmitters has been confirmed in the meantime (Reghunandanan V et al. 1998 *Indian. J. Exp. Biol.* 36: 635-43, Raggenbass M et al. 1998 *Prog Brain. Res.* 119: 263-273).

In the periphery the peptide hormones manifest their physiological action by binding to specific receptors, which are all derived from the large family of G protein-coupled 7-transmembrane helix receptors, but whose pharmacological profile as well as their intracellular "second messenger" differ (Michell R H et al. 1979 *Biochem. Soc. Trans.* 7:861-865; Thibonnier M et al. 1998 *Advantage. Exp. Med. Biol* 449: 251-276).

The principal physiological function of AVP consists in regulating the free water resorption in the kidneys and thus in maintaining the osmolarity of body fluids and blood volumes. The underlying antidiuretic action is mediated by binding of AVP to the renal $V_2$ receptor, which is expressed at the basolateral membrane of epithelial cells of the collecting tubule. After binding of AVP to the receptor, the G protein $G_S$ is bound intracellularly, which leads to the activation of adenylyl cyclase and to the synthesis of the second messenger cAMP. Following this protein kinase A is activated, which for its part phosphorylates proteins, which in turn leads primarily to the insertion of aquaporin-2 water channels (AQP-2) into the side of the cell membrane of the epithelial cells facing the interior of the collecting tubules. Secondarily the transcription of AQP-2 mRNA and the biosynthesis of this protein is induced (Hayashi M et al. 1994 *J. Clin. Invest.* 94:1778-1783). AQP-2 in the cell membrane leads to the resorption of water from urine into the organism. Thus, the urinary volume is reduced and the osmolarity of the urine increases. Without the resorption mechanism the loss of water would lead within a very short time to dehydration and death of the organism. The dissociation constant of AVP for the binding to the renal $V_2$ receptor is 0.4 nM (Lolait J L et al. 1992 *Nature* 357: 336-339).

A large number of further physiological functions of AVP are mediated via the binding to the $V_1$ receptor. The vascular $V_1$ receptor, which is localised on the surface of smooth vascular muscle cells of blood vessels, is involved in the regulation of the blood pressure by vasoconstriction after muscle contraction of the vascular muscle cells. After binding to the receptor and activation of coupled G proteins, the phospholipases C, D and $A_2$ are activated, which leads to the formation of the second messenger diacylglycerol and inositol triphosphate. Simultaneously various protein kinases are activated, leading to the mobilisation of intracellular calcium, to the inflow of extracellular calcium, and to the activation of a sodium $^+$-$H^+$ channel (Thibonnier M et al 2000 *Am. J. Physiol.* 279: H2529-2539).

The activation of the kinases leads to the activation of transcription factors in the cell nucleus, which after induction of immediate early response genes leads to an increase in the protein content and to cell proliferation (Geisterfer A A T et al 1989 *Hypertension* 14: 413-420). This mitogenic action of AVP was found, apart from smooth vascular muscle cells, also in various permanent cell lines and in mesangial kidney cells, hepatocytes and glomerular cells of the adrenal cortex.

Apart from the localisation in the blood vessels, the $V_1$ receptor is also found in the liver, where after AVP activation glycogenolysis occurs, in the adrenal cortex, where after AVP activation aldosterone is secreted, in the pancreas, where insulin secretion occurs, in the auricular myocardial cells in the heart, where the release of the atrial natriuretic factor occurs, in thrombocytes, where the aggregation of platelets occurs, in the spleen, in the kidneys, in the brain, in the uterus, in adipocytes and in various cell culture lines (Jard S 1998 In: Zingg H Het al eds 449: 1-13, Thibonnier M et al. 2001 *Annu. Rev. Pharmacal. Toxicol.* 41: 175-202). The dissociation constant for the binding of AVP to the vascular $V_1$ receptor is 1.2 nM (Thibonnier M et al. 1994 *J. Biol. Chem.* 269: 3304-3310). This receptor responds only at AVP concentrations at which the renal $V_2$ receptor is already fully activated.

A third vasopressin receptor $V_3$ is localised in the interior lobe of the hypophysis. In corticotrophic cells it mediates the secretion of the adrenocorticotrophic hormone (ACTH) after activation by AVP. The $V_3$ receptor can activate various signal transduction pathways, both the pathway via adenylyl cyclase with the formation of cAMP as second messenger, and also the pathway via phospholipase C, which leads to the mobilisation of intracellular calcium (Thibonnier M 1997 *Endocrinology* 138:4109-4122).

Oxytocin mediates its peripheral action by binding to the oxytocin receptor, which is localised in the uterus, in the ovaries, in the mammary gland and in the kidneys. Oxytocin activates secretion of milk in the breast, and during birth is actively involved in the contraction of the uterus. The oxytocin receptor, after binding of the ligand as well as the AVP $V_1$ receptor, induces the intracellular mobilisation of calcium.

Congestive heart failure (CHF) is characterised as the end stage of many different medical conditions, mainly caused by hypertension and by coronary heart disease (myocardial infarction, angina pectoris), characterised by a weak pumping capacity of the heart, which with increasing severity of the disease is accompanied by apnoea on strenuous exertion, water retention in the lungs and tissues, hyponatremia and breathing difficulties when resting. Apart from the elderly, those in particular affected include previous myocardial infarct patients. If untreated, the condition after its onset leads to death within a short time, since due to the hypertrophy of the heart muscle cells there is an ongoing cardiac connective tissue metaplasia, in which the efficiency of the heart increasingly falls. Once the cardiac function starts to fail, this leads to a neurohormonal counter-regulation, in which the sympathetic nervous system (SNS) and the renin-angiotensin-aldosterone system (RAAS) are activated, which immediately leads to a vasoconstriction. The cardiac output is thereby initially raised, but after a certain time the continuing vasoconstriction overloads the heart muscle, and the death of heart muscle cells and hypertrophing cells lead to the increasing connective tissue metaplasia of the heart muscles already referred to above.

A significantly raised AVP plasma level is also found in CHF, most probably caused by the activated renin-angiotensin-aldosterone system (angiotensin II stimulates AVP secretion) and the activated sympathetic nervous system, which stimulates the synthesis of AVP in the hypothalamus (Schrier R W et al 1998 *Adv. Exp. Med. Biol.* 449: 415-426, Schrier R W et al 1999 *N. Engl. J. Med.* 341: 577-585). The raised AVP plasma level leads to the intensified reverse resorption of water in the kidneys, with the aforementioned consequences for the patient.

Accordingly, the peptide hormone is an obvious target for new treatments for this medical condition, since with AVP receptor antagonists diuretic effects can be achieved, which by reducing the water load also decrease the peripheral vascular resistance and thus reduce the stress on the heart. The directly vasoconstricting action of AVP, which is probably responsible in a small part for congestive heart failure, could also be controlled with AVP antagonists. Moreover, there is evidence that AVP, on account of its mitogenic action, plays a direct role in the hypertrophic connective tissue transformation of the myocardium (Nakamura Y et al. 2000 *Eur. J. Pharmacol.* 391: 39-48). Thus, AVP antagonism could play a role not only in the short-term treatment of acute congestive heart failure, but by inhibiting AVP-mediated hypertrophy could in the long term improve the status of the myocardium.

There is therefore an urgent need for improved treatments, since CHF is the single most widespread myocardial disease, the frequency of which has increased in recent years and places an enormous strain on the healthcare system. Once the connection between congestive heart failure and the activated RAAS and SNS was recognised, the standard treatment at the time consisted in giving angiotensin-converting enzyme (ACE) inhibitors, which moderate the activated RAAS, and in giving β blockers, which suppress the activated SNS, as well as in administering diuretics, like thiazides, loop diuretics and potassium-saving diuretics. Although the probability of survival is significantly increased by the combination treatment, patients inevitably have to be rehospitalised, so that there is a great need for improved treatment. The long term administration of diuretics can damage the kidneys and lead to disturbances in the electrolyte balance.

New approaches to the treatment of CHF, which are targeted directly on the action of AVP, are based on using receptor antagonists against the $V_1$ and $V_2$ receptors mentioned above (Lee C R 2003 *Am. Heart J.* 146: 9-18). A range of non-peptide receptor antagonists of the benzazepine group exist, which can be administered orally and bind with a high affinity (inhibition constants $K_i$ of 0.5 nM-3 nM, Thibonnier M et al. 2001 *Annu. Rev. Pharmacol. Toxicol.* 41: 175-202) either specifically to one or to both $V_1$ and $V_2$ receptors. Some of the receptor antagonists are undergoing further development after successful animal studies and small clinical studies.

The $V_2$ receptor antagonist Tolvaptan showed in a placebo-controlled double-blind study on CHF patients, who were receiving at the same time the standard treatment, a marked reduction in oedema and weight loss in patients with raised water retention (Gheorghiade M et al. 2000 *Circulation* 102: 592). In patients with hyponatremia there was a normalisation of the sodium concentration in the plasma (Gheorgbiade M et al. 2002 *J. Am. Coll. Cardiol.* 39: 171).

The most widely developed $V_1/V_2$ receptor antagonist Conivaptan has also proved effective in CHF patients. The decrease in the so-called "pulmonary capillary wedge pressure" after single intravenous administration indicates reduced stress on the heart. In addition, an increase in the amount of urine with a drop in the urine osmolarity after treatment with Conivaptan was recorded (Udelson J E et al. 2001 *Circulation* 104: 2417-2423).

A possibly positive effect of Conivaptan on cardiac hypertrophy occurring in CHF patients was demonstrated in cell culture studies in primary heart muscle cells, where the protein synthesis induced by AVP via the $V_1$ receptor could be inhibited in a dose-dependent manner (Tahara A et al. 1998 *Cardiovasc. Res.* 38: 198-205).

Data and studies on the safety, morbidity and mortality after long-term treatment of CHF patients with the AVP receptor antagonists are still not available, which means that the true value of the positive effects for the treatment of congestive heart failure found in the previous studies cannot be properly evaluated (Russel S D 2003 *Am. J. Cardiovasc. Drugs* 3: 13-20).

The object of the present invention is accordingly to provide an agent for treating conditions that are attributed to or are caused by a raised AVP plasma level. A further object of the present invention is to provide as an alternative to AVP receptor antagonists new AVP antagonists that can be used in particular as an alternative to AVP receptor antagonists. Yet a further object of the present invention is to provide antagonists with a high specificity for AVP.

In a first aspect the object of the invention is achieved by a vasopressin antagonist, in which the antagonist is a nucleic acid. In a preferred embodiment the nucleic acid is a vasopressin-binding nucleic acid, in particular a L-nucleic acid. In a further embodiment the vasopressin is the human vasopressin described herein. In yet a further embodiment the nucleic acid is one that has been disclosed herein in connection with the various aspects of the present invention. In a further embodiment this nucleic acid according to the first aspect of the present invention comprises one or more of the features that are described in connection with the various aspects of the present invention.

In a second aspect the object of the invention is achieved by an antagonist of a vasopressin receptor system, in which the antagonist is a nucleic acid that preferably manifests its action by binding to the ligand (Arg$^8$)-vasopressin. In one embodiment the nucleic acid comprises at least one L-nucleotide, and preferably the nucleic acid comprises a L-nucleic acid. In a further embodiment the nucleic acid is one that has been disclosed herein in connection with the various aspects of the present invention. In yet a further embodiment this nucleic acid according to the first aspect of the present invention comprises one or more of the features that have been described in connection with the various aspects of the present invention. In a preferred embodiment the vasopressin receptor system is the vasopressin receptor $V_2$ (Lolait J L et al. 1992 *Nature* 357: 336-339), the vasopressin receptor $V_1$ (Thibonnier M et al. 1994 *J. Biol. Chem.* 269:3304-3310), or the vasopressin receptor $V_3$ (Thibonnier M 1997 *Endocrinology* 138:4109-4122).

In a second aspect the object is achieved by a vasopressin-binding nucleic acid, in which the nucleic acid contains a stretch Box1 and a stretch Box2,
   in which Box1 comprises the sequence GUGGW and W=A or U, preferably W=U, and
   in which Box2 comprises a sequence of about 18 to 24 nucleotides, preferably comprises 21 nucleotides, and a group $(G)_n$ is contained 4 times in the sequence, wherein n=2, 3 or 4.

In an embodiment of the third aspect it is envisaged that in the first group $(G)_n$ in the 5'-3'-direction n=4, in the second group (G)$_n$ in the 5'-3'-direction n=3, in the third group (G)$_n$ in the 5'-3'-direction n=2, and in the fourth group (G)$_n$ in the 5'-3'-direction n=3.

In an embodiment of the third aspect it is envisaged that Box2 comprises the sequence

GGGGUAGGGMUUGGAHGGGHA, (SEQ ID NO: 50)

in which
M in each case and independently is A or C, and
H in each case and independently is A, C or U.

In a preferred embodiment of the third aspect it is envisaged that U or C, preferably U, is present at the positions of H.

In an embodiment of the third aspect it is envisaged that the nucleic acid comprises a stretch Helix1 and a stretch Helix2, in which Helix1 and Helix2 in each case contain 5 to 9 nucleotides, preferably 6 to 7 nucleotides and more preferably 7 nucleotides, and the stretches Helix1 and Helix2 are complementary to one another and preferably form a double-stranded helix.

In a preferred embodiment of the third aspect it is envisaged that the double-stranded helix is terminally formed.

In an embodiment of the third aspect it is envisaged that the nucleic acids comprise a W stretch, in which the W stretch contains 0 to 10, preferably 6 to 9 nucleotides, or alternatively 0 to 7 nucleotides.

In a preferred embodiment of the third aspect it is envisaged that the W stretch consists either (a) only of one or more of A and/or U, or consists (b) of one or more of A and/or U and a G.

Box2 is a sequence of about 18 to about 24 nucleotides, preferably 21 nucleotides, and the group (G)$_n$ is contained four times in the sequence of Box2, wherein n=2, 3 or 4.

As can be seen from the Formula (I), the nucleic acids according to the invention have in one embodiment a consensus structure. The consensus structure comprises in this connection two complementary regions, named Helix1 at the 5'-end and Helix2 at the 3'-end, which as a result of the primary structure of the nucleic acid pair with one another and form a terminal, double-stranded helix within the consensus structure. More preferably the helix has a length of 7 paired nucleotides. In the 5'-3'-direction the first complementary region is followed by a Box1, which preferably consists of five nucleotides of the sequence GUGGW, in which W denotes A or U, wherein preferably a U is present at this position. This sequence is followed by a six to nine nucleotide long A-rich and U-rich region, termed a W stretch, in which W is predominantly present, G is rarely present and C is never present. This is then followed by a twenty-one nucleotide long Box2, which preferably has the following sequence, namely GGGGUAGGGMUUGGAHGGGHA (SEQ ID NO: 50), in which M denotes A or C, and H denotes A or C or U, wherein at the positions where H is present it preferably denotes U or C, and more preferably denotes U. A characteristic feature of Box2 are four strictly conserved Gs occurring twice to four times. This is followed in the 5'-3'-direction by the second complementary region, named Helix2, which with the complementary region at the 5'-end forms the terminal, double-stranded helix.

Formula (I) (SEQ ID NO: 51)

Consensus: 5'- [Helix1] - [Box1] -WWDWDDWWW- [Box2] - [Helix2] -3'
7 nt    GUGGW    6-9 nt    GGGGUAGGGMUUGGAHGGGHA    7 nt In an embodiment of the third aspect it is envisaged that the W stretch contains a PEG group.

In a preferred embodiment of the third aspect it is envisaged that the PEG group is at the 5'-end of the W stretch or at the 3'-end of the W stretch or between two nucleotides of the W stretch.

In an embodiment of the third aspect it is envisaged that the nucleic acid contains a PEG group.

In a fourth aspect the object is achieved by a nucleic acid, preferably a nucleic acid according to the first, second or third aspect, according to the Formula (I)

(Formula I)

5'- [Helix1] - [Box1] -WWDWDDWWW- [Box2] -[Helix2] -3' wherein
Helix1 contains 7 nucleotides
Helix2 contains 7 nucleotides
Helix1 and Helix2 are complementary to one another and form a terminal double-stranded helix
Box1 is GUGGW, in which W A or U, preferably is U,
The W stretch WWDWDDWWW contains 6 to 9 nucleotides, in which
D individually and independently may be A, G or U, and in which preferably the W stretch consists either (a) only of one or more of A and/or U, or consists (b) of one or more of A and/or U and a G.

In a fifth aspect the object is achieved by a nucleic acid, preferably by a nucleic acid according to the first, second or third aspect, according to Formula (II)

(II)

5'- [Helix1] - [Box1] -[(W)$_t$ [- - -] (W)$_u$]- [Box2] - [Helix2] -3' in which [⋯] denotes a PEG group,
t and u individually and independently of one another are 0, 1, 2, 3, 4 or 5, wherein t+u is 0, 1, 2, 3, 4 or 5; and
in which
Helix1, Helix2, Box1 and Box2 are defined as in connection with the fourth aspect; and
W=A or U.

As can be seen from the Formula (II), the nucleic acids according to the invention in one embodiment have a consensus structure as in Formula (I), with the difference that the A-rich and U-rich stretch between Box1 and Box2 consist of a PEG-(hexaethylene glycol) spacer in combination with zero to five Ws, and the position of the PEG spacer in the A-rich and U-rich stretch is freely variable. In the nucleic acids according to the invention according to Formula (II) this stretch is called PEG+W.

Formula (II) (SEQ ID NOS 52 & 53, respectively)

Consensus: 5'- [Helix1] - [Box1] -W --- WWW- [Box2] - [Helix2] -3'
            7 nt    GUGGW   PEG + W   GGGGUAGGGMUUGGAHGGGHA    7 nt ---: PEG spacer In a sixth aspect the object is achieved by a nucleic acid, preferably a nucleic acid according to the first, second or third aspect, according to the Formula (III)

5'-WWWWWWW- [Box2] - [Helix2] - ▓▓▓ - [Helix1] - [Box1] -3'  (III)

in which ▓▓▓ denotes a PEG group, and
in which
  Helix1 and Helix2 in each case contain 6 or 7 nucleotides, preferably 6 nucleotides,
  Helix1 and Helix2 are complementary to one another and form a double-stranded Helix,
  Box1 and Box2 are defined as in connection with the fourth aspect, in which the W stretch WWWWWWW consists of 0 to 7 Ws, in which W=A or U, and preferably no W is present in Formula (III), and the PEG group in the 5'-3'-direction is between Helix2 and Helix1.

As can be seen from the Formula (III), nucleic acids according to the invention comprise in one embodiment a consensus structure as in Formula (II), but with the following differences. The position of the 5'-end and 3'-end is changed inasmuch as the 5'-end of the nucleic acids according to the invention lies in the A-rich and U-rich stretch, and the 3'-end is localised at the end of Box1. The W stretch consists of zero to seven Ws, preferably of zero W. Box1 and Box2 comprise the sequences illustrated in the Formulae (I) and (II), consisting of five and twenty-one nucleotides. The complementary regions Helix1 and Helix2 consist of in each case six or seven nucleotides, preferably of six nucleotides, which form a double-stranded helix. The PEG spacer no longer lies in the A-rich and U-rich stretch, but instead looking in the 5'-3'-direction, is located between the end of Helix2 and the start of Helix1. Helix1 is followed by Box1, the 3'-end of which, as already mentioned, forms the 3'-terminus of the nucleic acids according to the invention.

Formula (III) (SEQ ID NOS: 54 & 55, respectively)

Consensus: 5'-WWWWWWW- [Box2] - [Helix2] - --- - [Helix1] - [Box1] -3'
            0-7 nt    GGGGUAGGGMUUGGAHGGGHA    6-7 nt         6-7 nt    GUGGW ---: PEG-Spacer
---: PEG spacer The nucleic acids according to the invention also include the nucleic acids listed in the following table, which are also identified herein as nucleic acids according to the invention. The abbreviations and symbols used in this connection correspond to those defined herein.

| Internal Identification | Sequence | SEQ. ID: No. |
|---|---|---|
| CHF-134-A9 | AGCGUGC GUGGA AA-UUAUAU GGGGUAGGGCUUGGAUGGGUA GUACGCU | 2 |
| CHF-157-A2 | AGUACGC GUGGU AAAUUGAAU GGGGUAGGGCUUGGAUGGGUA GUGUACU | 3 |
| CHF-157-H3 | AGGACGC GUGGU AA-UUAUAU GGGGUAGGGCUUGGAUGGGUA GUGUCCU | 4 |
| CHF-157-C4 | AGUAUGC GUGGU AAAUUAAAU GGGGUAGGGCUUGGAUGGGUA GUGUACU | 5 |
| CHF-157-A4 | AGUAUGC GUGGU AAAUGAU-U GGGGUAGGGCUUGGAUGGGUA GUGUACU | 6 |
| CHF-157-G3 | AGUAUGC GUGGU AAAUGAU-U GGGGUAGGGCUUGAAUUGGUA GUGUACU | 7 |
| CHF-157-H1 | AGUAUGC GUGGU AUAU--AAU GGGGUAGGGCUUGGAUGGGUA GUGUACU | 8 |
| CHF-157-B2 | AGUACGC GUGGU U--UAAAAU GGGGUAGGGCUUGGAUGGGUA GUGUACU | 9 |
| CHF-157-C1, C2 | AGUCUGC GUGGU UUUUU-AAU GGGGUAGGGCUUGGAUGGGUA GUAGACU | 10 |
| CHF-157-E1 | AGUCUGC GUGGU UUUUUU-AU GGGGUAGGGCUUGGAUGGGUA GUAGACU | 11 |
| CHF-157-C3 | AGUCUGC GUGGU UUUUAAAUU GGGGUAGGGCUUGGAUGGGUA GUAGACU | 12 |

-continued

| Internal Identification | Sequence | SEQ. ID: No. |
|---|---|---|
| CHF-157-B3 | AGUAUGC GUGGU UUUU--AAU GGGGUAGGGCUUGGAUGGGUA GUAUACU | 13 |
| CHF-157-A3 | AGUGUGC GUGGU UAG---AAU GGGGUAGGGCUUGGAUGGGUA GUACACU | 14 |
| CHF-157-B4 | AGUGUGC GUGGU UAAU--AAU GGGGUAGGGCUUGGAUGGGUA GUACACU | 15 |
| CHF-157-E2, E3 | AGUGUGG GUGGU UAAU--AAU GGGGUAGGGCUUGGAUGGGUA CCACACU | 16 |
| CHF-157-D2 | AGUAUGG GUGGU UAUU--AAU GGGGUAGGGCUUGGAUGGGUA CCAUACU | 17 |
| CHF-157-D1 | AGUAACC GUGGU UUA---AAU GGGGUAGGGAUUGGAUGGGCA GGAUACU | 18 |
| CHF-157-G2 | AGUAGCC GUGGU UUA---AAU GGGGUAGGGAUUGGAUGGGCA GGAUACU | 19 |
| CHF-157-D3 | AGUGACC GUGGU AAAU--AAU GGGGUAGGGAUUGGAUGGGCA GGACACU | 20 |
| CHF-157-F3 | AGUGACC GUGGU AAAU--GAU GGGGUAGGGAUUGGAUGGGCU GGACACU | 21 |
| CHF-157-F1, G1 | AGUGACC GUGGU AAAU--AUU GGGGUAGGGAUUGGAUGGGCA GGACACU | 22 |
| CHF-157-D4 | AGUAUGC GUGGU AAAU--AGU GGGGUAGGGAUUGGAUGGGCA GUAUACU | 23 |
| CHF-F-000 | AGUGUGC GUGGU UAAUAAU GGGGUAGGGCUUGGAUGGGUA GUACACU | 24 |
| CHF-F-002 | AGUGUGC GUGG ---AUAAU GGGGUAGGGCUUGGAUGGGUA GUACACU | 25 & 56 |
| CHF-F-003 | AGUGUGC GUGGU ---UAAU GGGGUAGGGCUUGGAUGGGUA GUACACU | 26 & 57 |
| CHF-F-004 | AGUGUGC GUGGU U---AAU GGGGUAGGGCUUGGAUGGGUA GUACACU | 27 & 58 |
| CHF-F-005 | AGUGUGC GUGGU UA---AU GGGGUAGGGCUUGGAUGGGUA GUACACU | 28 & 59 |
| CHF-F-005 | AGUGUGC GUGGU UAA---U GGGGUAGGGCUUGGAUGGGUA GUACACU | 29 & 60 |
| CHF-F-007 | AGUGUGC GUGGU UAAU--- GGGGUAGGGCUUGGAUGGGUA GUACACU | 30 & 61 |
| CHF-F-010 | AGUGUGC GUGGU ------U GGGGUAGGGCUUGGAUGGGUA GUACACU | 26 & 31 |
| CHF-F-011 | AGUGUGC GUGGU --- AAU GGGGUAGGGCUUGGAUGGGUA GUACACU | 26 & 32 |
| CHF-F-019 | AGUGUGC GUGGU ---  AU GGGGUAGGGCUUGGAUGGGUA GUACACU | 26 & 33 |
| CHF-F-020 | AGUGUGC GUGGU ---    U GGGGUAGGGCUUGGAUGGGUA GUACACU | 26 & 34 |
| CHF-F-021 | AGUGUGC GUGGU ---      GGGGUAGGGCUUGGAUGGGUA GUACACU | 26 & 35 |
| CHF-F-003 | AGUGUGC GUGGU ---UAAU GGGGUAGGGCUUGGAUGGGUA GUACACU | 26 & 36 |
| CHF-F-011 | AGUGUGC GUGGU --- AAU GGGGUAGGGCUUGGAUGGGUA GUACACU | 26 & 37 |
| CHF-F-001 | AAUAAU GGGGUAGGGCUUGGAUGGGUA GUACACU ---AGUGUGC GUGGU U | 38 & 62 |
| CHF-F-014 | UAAUAAU GGGGUAGGGCUUGGAUGGGUA GUACACU ---AGUGUGC GUGGU | 39 & 63 |
| CHF-F-015 | UAAU GGGGUAGGGCUUGGAUGGGUA GUACACU ---AGUGUGC GUGGU | 40 & 63 |
| CHF-F-016 | AAU GGGGUAGGGCUUGGAUGGGUA GUACACU ---AGUGUGC GUGGU | 41 & 63 |
| CHF-F-017 | AU GGGGUAGGGCUUGGAUGGGUA GUACACU ---AGUGUGC GUGGU | 42 & 63 |
| CHF-F-018 | U GGGGUAGGGCUUGGAUGGGUA GUACACU ---AGUGUGC GUGGU | 43 & 63 |
| CHF-F-032 | U GGGGUAGGGCUUGGAUGGGUA GUACACU ---AGUGUGC GUGG | 43 & 44 |
| CHF-F-033 | GGGGUAGGGCUUGGAUGGGUA GUACACU ---AGUGUGC GUGGU | 45 & 63 |
| CHF-F-034 | GGGGUAGGGCUUGGAUGGGUA GUACACU ---AGUGUGC GUGG | 45 & 46 |
| CHF-F-035 | U GGGGUAGGGCUUGGAUGGGUA GUACAC --- GUGUGC GUGGU | 64 & 47 |
| CHF-F-036 | U GGGGUAGGGCUUGGAUGGGUA GUACAC --- GUGUGC GUGG | 64 & 48 |
| CHF-F-037 | GGGGUAGGGCUUGGAUGGGUA GUACAC --- GUGUGC GUGGU | 49 & 47 |
| CHF-F-038 | GGGGUAGGGCUUGGAUGGGUA GUACAC --- GUGUGC GUGG | 49 & 48 | in which --- denotes a PEG group, as defined herein, for the sequences presented below CHF-F-000.

In an embodiment of the sixth aspect it is envisaged that in the first group $(G)_n$ in the 5'-3'-direction n=4, in the second group $(G)_n$ in the 5'-3'-direction n=3, in the third group $(G)_n$ in the 5'-3'-direction n=2, and in the fourth group $(G)_n$ in the 5'-3'-direction n=3.

In an embodiment of the first to sixth aspect, in particular of the fourth to sixth aspect, it is envisaged that the PEG group has a molecular weight of about 172-688 Da, preferably about 344.

In an embodiment of the first to sixth aspect it is envisaged that the sequence is selected from the group of sequences comprising SEQ ID NOS 2-24, 25 & 56, 26 & 57, 27 & 58, 28 & 59, 29 & 60, 30 & 61, 26 & 31, 26 & 32, 26 & 33, 26 & 34, 26 & 35, 26 & 36, 26 & 37, 38 & 62, 39 & 63, 40 & 63, 41 & 63, 42 & 63, 43 & 63, 43 & 44, 45 & 63, 45 & 46, 64 & 47, 64 & 48, 49 & 47, and 49 & 48.

In an embodiment of the fourth to sixth aspect it is envisaged that the nucleic acid binds to vasopressin.

In a preferred embodiment it is envisaged that the vasopressin is human vasopressin.

In an embodiment of the first to sixth aspect it is envisaged that the vasopressin has an amino acid sequence according to SEQ. ID. NO. 1.

In an embodiment of the first to sixth aspect it is envisaged that the nucleic acid comprises a modification.

In a preferred embodiment it is envisaged that the modification is selected from the group comprising HESylation and PEGylation.

In a preferred embodiment it is envisaged that the PEGylation is effected by a straight-chain or branched PEG, in which the molecular weight of the PEG is about 20 to 100 kDa, preferably about 30 to 80 kDa, and more preferably about 40 kDa.

In a preferred embodiment it is envisaged that the HESylation is effected by a HES, in which the molecular weight of the HES is about 10 to 130 kDa, preferably about 30 to 80 kDa and more preferably about 50 kDa.

In an embodiment of the first to sixth aspect it is envisaged that the nucleic acid consists completely of L-nucleotides.

In a seventh aspect the object is achieved by a pharmaceutical composition comprising a nucleic acid according to one of the aspects one to six and optionally a further constituent, in which the further constituent is selected from the group comprising pharmaceutically acceptable carriers.

In an eighth aspect the object is achieved by the use of a nucleic acid according to one of the aspects one to six for the production of a medicament.

In a ninth aspect the object is achieved by the use of a nucleic acid according to one of the aspects one to six for the production of a diagnostic agent.

In an embodiment of the ninth aspect it is envisaged that the medicament is for the treatment and/or prevention of congestive heart failure, preferably for the short-term treatment, and more preferably for the treatment and/or prevention of acute decompensated congestive heart failure.

In an alternative embodiment of the ninth aspect it is envisaged that the medicament is for the treatment and/or prevention of an illness, in which the illness is a sequela of a condition that is selected from the group comprising hypertension, coronary heart disease, myocardial infarction and angina pectoris.

In an embodiment of the ninth aspect it is envisaged that the patient is an elderly person or patient who has previously had a myocarcial infarction.

In an alternative embodiment of the ninth aspect it is envisaged that the medicament is a medicament for the prevention and/or treatment of hypertension.

In a further alternative embodiment of the ninth aspect it is envisaged that the medicament is a medicament for the treatment and/or prevention of hypertrophy of the heart muscle, more particularly hypertrophy of the heart muscle mediated by (arginine$^8$)-vasopressin.

In an embodiment of the ninth aspect it is envisaged that the medicament is a medicament for the treatment and/or prevention of oedema.

In an embodiment of the ninth aspect it is envisaged that the medicament is a medicament for reducing the weight of patients with raised water retention.

In an embodiment of the ninth aspect it is envisaged that the medicament is a medicament for treating persons with hyponatremia or for preventing hyponatremia.

In an embodiment of the ninth aspect it is envisaged that the medicament is a medicament for the treatment and/or prevention of the syndrome of inadequate ADH secretion.

In a preferred embodiment of the ninth aspect it is envisaged that the syndrome of inadequate ADH secretion is accompanied by at least one further symptom, in which the further symptom is selected from the group comprising antidiuresis, hyponatremia and hypoosmolarity.

In an embodiment of the ninth aspect it is envisaged that the syndrome of inadequate ADH secretion has at least one cause, in which the cause is selected from the group comprising ectopic ADH secretion by tumours, drug-induced ADH secretion, pulmonary disease, and changes in the central osmoreceptors after cranial-cerebral trauma or after meningitis.

In an alternative embodiment of the ninth aspect it is envisaged that the medicament is a medicament for the prevention and/or treatment of hyponatremia associated with cirrhosis of the liver.

In an alternative embodiment of the ninth aspect it is envisaged that the medicament is a medicament for the treatment and/or prevention of cerebral oedema, in particular after cranial-cerebral trauma or after a stroke.

In an alternative embodiment of the ninth aspect it is envisaged that the medicament is for the treatment and/or prevention of cranial-cerebral trauma and/or stroke.

In an alternative embodiment of the ninth aspect it is envisaged that the medicament is a medicament for the treatment and/or prevention of a tumour.

In a preferred embodiment of the ninth aspect it is envisaged that at least some of the cells forming the tumour express at least one receptor, in which the receptor is selected from the group comprising $V_1$ receptors, $V_2$ receptors and $V_3$ receptors.

In a further preferred embodiment of the ninth aspect it is envisaged that the tumour is selected from the group comprising ACTH-secreting tumours, small cell bronchial carcinoma and breast cancer.

In an alternative embodiment of the ninth aspect it is envisaged that the medicament is a medicament for preventing premature births.

In a further alternative embodiment of the ninth aspect it is envisaged that the medicament is for preventing and/or treating primary dysmenorrhoea.

In a tenth aspect the object is achieved by a complex comprising vasopressin and a nucleic acid according to one of the aspects one to six.

In an eleventh aspect the object is achieved by a complex comprising oxytocin and a nucleic acid according to one of the aspects one to six.

In a twelfth aspect the object is achieved by methods for screening vasopressin antagonists or vasopressin agonists, comprising the following steps:

provision of a candidate vasopressin antagonist and/or a candidate vasopressin agonist, provision of a nucleic acid according to one of the aspects one to six, provision of a test system which produces a change of signal in the presence of a vasopressin antagonist and/or a vasopressin agonist, and determination of whether the candidate vasopressin antagonist is a vasopressin antagonist, and/or whether the candidate vasopressin agonist is a vasopressin agonist.

In an embodiment it is envisaged that the vasopressin is (arginine$^8$)-vasopressin.

In a thirteenth aspect the invention is achieved by methods for screening vasopressin agonists and/or vasopressin antagonists, comprising the following steps:

provision of vasopressin in a phase, preferably a solid phase, provision of a nucleic acid according to one of the aspects one to six, preferably a labeled nucleic acid according to one of the aspects one to six, addition of a candidate vasopressin agonist and/or a candidate vasopressin antagonist, and determination of whether the candidate vasopressin agonist is a vasopressin agonist and/or whether the candidate vasopressin antagonist is a vasopressin antagonist.

In an embodiment it is envisaged that the determination is carried out by establishing whether the nucleic acid is displaced by the candidate vasopressin agonist.

In a fourteenth aspect the object is achieved by a kit for the detection of vasopressin and/or oxytocin, preferably arginine-vasopressin, comprising a nucleic acid according to one of the aspects one to six.

The inventors have surprisingly found that it is possible to screen nucleic acids, and in particular L-nucleic acids, binding specifically to (Arg$^8$)-vasopressin. The nucleic acids according to the invention are preferably ribonucleic acids and more preferably L-ribonucleic acids. The (Arg$^8$)-vasopressin-binding nucleic acid molecules according to the invention constitute a surprising improvement compared to the vasopressin-binding DNA molecule described in the prior art (Williams K. P. et al. 1997 *Proc. Natl. Acad. Sci USA* 94: 11285-11290), in that the DNA molecule described in the prior art only had a dissociation constant of 0.9 μM in vitro. In cell culture tests this DNA molecule of the prior art had an IC50 of approx. 3 μM and was therefore discounted as a possible promising therapeutic agent on account of its poor binding to vasopressin. Finally, the (Arg$^8$)-vasopressin-binding DNA molecule according to the prior art was also not advantageous compared to the nucleic acids according to the invention, since it has a length of 55 nucleotides, which would have involved a considerable production effort and expenditure. Compared to this the nucleic acids according to the invention have an improved affinity that is better by several orders of magnitude (dissociation constant: 1.5 nM, measured by isothermal calorimetry; IC50: 1 nM in the cAMP cell culture test), are shorter by up to 17 nucleotides and, as is shown in more detail in the example, are also active in vivo and at 37° C. To this extent the present inventors have disproved the generally held opinion of specialists, based on the prior art, that (Arg$^8$)-vasopressin-binding nucleic acids are not suitable for therapeutic purposes.

In addition the present inventors have surprisingly established that all positive effects that have hitherto been demonstrated with AVP receptor antagonists, such as for example raised diuresis without disturbing the electrolyte balance, reducing cardiac stress, or possibly inhibiting hypertrophy of the heart muscle, can also be achieved with the compounds according to the invention.

A further advantage of the nucleic acids according to the invention consists in that, compared to AVP receptor antagonists according to the prior art, they are advantageous for long term medication. In the medication with AVP receptor antagonists according to the prior art a counter-regulation accompanied by a rise in the AVP concentration in the plasma may occur, which in the case of long term medication may ultimately reduce the effects of the antagonists. Even if this reaction were to occur when using the nucleic acids according to the invention, a correspondingly high dosage can itself neutralise unphysiologically high AVP plasma levels.

The nucleic acids according to the invention comprise in a preferred embodiment also those nucleic acids that are substantially homologous to the sequences specifically disclosed herein. The term "substantially homologous" shall preferably be understood to mean herein that the homology is at least 75%, preferably 85%, more preferably 90% and most particularly preferably more than 95, 96, 97, 98 or 99%.

The nucleic acids according to the invention are preferably those consisting of ribonucleotides. It is however also possible within the scope of the present invention for individual nucleotides to be present in the molecule as 2'-deoxyribonucleotides or other variants, such as for example 2'-O-methylribonucleotides, or LNA nucleotides. It is most preferred however if the nucleic acid consists completely of ribonucleotides.

The nucleic acids according to the invention preferably bind to vasopressin at 37° C. in solution with a dissociation constant Kd<10 nM, measured by isothermal calorimetry.

The nucleic acids according to the invention may in a preferred embodiment also bind to oxytocin.

Within the scope of the present invention, in one embodiment the nucleic acids according to the invention also comprise those that are part of a longer nucleic acid, in which these longer nucleic acids may comprise several parts, at least one part being a nucleic acid according to the present invention, or a part thereof. The other part or the other parts of these longer nucleic acids may either be a D-nucleic acid or a L-nucleic acid. Each and any combination may be used in conjunction with the present invention and for the purposes and uses as are disclosed herein for the nucleic acids according to the invention. This other part or these other parts of the longer nucleic acid may have a function that is different from binding, and in particular different from binding to vasopressin and/or oxytocin. A possible function is to permit an interaction with other molecules, e.g. for the purposes of immobilisation, crosslinking, detection, amplification or modification, or to increase the molecular weight.

In a further aspect the present invention relates to a pharmaceutical composition which consists of at least one of the nucleic acids according to the invention in combination with one or more other nucleic acids, in which the other nucleic acid or acids preferably binds to target molecules other than (Arg$^8$)-vasopressin, or exerts a function different to that of the nucleic acids according to the invention.

In an embodiment the nucleic acids according to the invention are present in modified form. Particularly preferred forms of modification are PEGylation or HESylation. This involves the modification of the nucleic acids according to the invention by binding of polyethylene glycol (PEG), hydroxyethyl starch (HES) or other groups, which have been described in European Patent Application EP 1 306 382 and the disclosures of which are referred to and incorporated herein.

Preferably the molecular weight of the nucleic acid according to the invention modified in this way, i.e. PEGylated, is about 2,000 to 200,000 Da., preferably 40,000 to 120,000 Da.

The HESylation of nucleic acids is described for example in the German Patent Application DE 1 2004 006 249.8. The hydroxyethyl starch (HES) used in this connection preferably has a number average molecular weight of 3 to 100,000 Da, and more preferably 5,000 to 60,000 Da.

The advantage of modifying the nucleic acid according to the invention using high molecular weight polymers which are physiologically acceptable, such as for example hydroxyethyl starch (HES) or polyethylene glycol (PEG), is that the excretion kinetics of the nucleic acids according to the invention is altered. Without wishing to be bound by any theory, this behaviour of the nucleic acids according to the invention that have been modified in this way appears to be based on the fact that, as a result of the increased molecular weight of the thereby modified nucleic acids according to the invention and their lowered metabolic activity, in particular if these acids are present as L-nucleic acids, their excretion from an organism, in particular a mammalian organism, is slowed down. Since the excretion typically takes place via the kidneys, it is assumed at the present time that the glomerular filtration rate of the kidneys as regards the nucleic acids according to the invention that have been modified in this way is significantly reduced compared to that of the unmodified nucleic acids according to the invention, which leads to an increased residence time, i.e. biological half-life of the modified nucleic acids according to the invention, in particular of the modified L-nucleic acid according to the invention, compared to the residence time of the corresponding, but unmodified nucleic acids according to the invention, especially the unmodified L-nucleic acids. Particularly noticeable in this connection is the fact that, despite the modification present in a preferred embodiment, the nucleic acids according to the invention modified in this way do not obviously lose their specificity. Accordingly the nucleic acids according to the invention, especially in their modified form, completely surprisingly exhibit a property that normally cannot otherwise be realised in other pharmaceutically active compounds, namely that extensive galenical formulations, for example in the form of depot preparations, that successively release the active constituent can be omitted, and instead a direct modification of the active constituent in question can be implemented without its biological activity, expressed in particular as the specificity of the reaction or complex formation with the respective target molecule, being adversely affected. It is within the scope of the present invention to employ the modified nucleic acids according to the invention in the form of depot preparations.

It is also within the scope of the present invention for the nucleic acids according to the invention to be present in unmodified form, i.e. to contain no modification, which reduces the effort and expenditure involved in their production. Especially in the treatment of acute decompensated congestive heart failure in intensive care treatment involving intravenous infusion, this embodiment of the nucleic acids according to the invention is particularly advantageous insofar as the dosage can be better controlled and it can be used in cases where a rapid excretion through diuresis or a short half-life in the plasma is desired.

As a result of the high stability of the nucleic acids according to the invention, especially in the embodiment where these are present as L-nucleic acids, a direct administration of the nucleic acids according to the invention to treat a patient who requires such a treatment is possible. Preferably the nucleic acids according to the invention are available as a physiological solution for topical or systemic application. Preferably the pharmaceutical composition is for intravenous application. It is however also possible within the scope of the present invention for such pharmaceutical compositions to be administered intramuscularly, intraperitoneally, or subcutaneously. The nucleic acids according to the invention are preferably contained or dissolved in a pharmaceutically acceptable solvent. Such solvents are in particular those that are selected from the group comprising physiological saline solution, PBS, or a glucose solution, in particular a 5% glucose solution.

The nucleic acids according to the invention may be used to produce a medicament as well as to produce a diagnostic agent. The diagnostic application or use is based in this connection on the specific interaction between the nucleic acids according to the invention and vasopressin, in particular $(Arg^8)$-vasopressin and/or oxytocin, which in their totality or individually are also denoted herein as target molecule. As a result of the involvement of vasopressin and/or oxytocin in the various conditions and diseases described herein in connection with the aspect of the use of the nucleic acids according to the invention for the production of a medicament, a definitive diagnosis of such conditions is possible within the scope of the present invention using the nucleic acids according to the invention. In the context of a corresponding diagnostic procedure, the concentration of the target molecule is preferably determined by the interaction with one or more of the nucleic acids according to the invention. Such an interaction can for example be detected by the fact that in a competitive test assay for determining the concentration of $(Arg^8)$-vasopressin in body fluids, the binding of a labeled vasopressin tracer to the nucleic acid according to the invention is in competition with the $(Arg^8)$-vasopressin originating from the body fluid.

The conditions for the treatment of which the nucleic acids according to the invention can be used are directly or indirectly connected with a raised vasopressin level in the organism to be treated, in particular a mammal and preferably a human compared to normal physiological conditions. Preferably the raised vasopressin level is a raised titre of vasopressin in a body fluid, the body fluid preferably being blood.

A condition for the treatment of which the nucleic acids according to the invention can be used is CHF. In this case it is within the scope of the present invention to use the nucleic acids according to the invention for the short-term treatment of congestive heart failure. A further type of heart failure to be treated or prevented by means of the nucleic acids according to the invention is acute decompensated congestive heart failure.

It is also within the scope of the present invention to use the nucleic acids according to the invention to treat hypertension, coronary heart disease, myocardial infarction and angina pectoris. In a particularly preferred embodiment hypertension, coronary heart disease, myocardial infarction and angina pectoris are conditions which ultimately lead to congestive heart failure, which to this extent may constitute the end stage of these conditions. In a preferred embodiment congestive heart failure in the embodiments described herein as well as the other mentioned conditions, in particular coronary heart disease, myocardial infarction, angina pectoris and hypertension, is a condition that occurs especially in elderly patients or in patients who have suffered one or more myocardial infarctions. In a preferred embodiment elderly patients are in particular those whose bodily capacity/performance compared to the maximum capacity/performance is reduced due to age.

Further medical conditions in which the medicaments according to the invention can be used for treatment and/or prevention include hypertrophy of the heart muscle, in particular hypertrophy of the heart muscle, oedema, and hyponatremia mediated by arginine-vasopressin.

A further condition that can be treated or prevented using the nucleic acids according to the invention is the syndrome of inadequate ADH secretion.

In the syndrome of inadequate ADH secretion (SIADH, Schwartz-Bartter Syndrome) the AVP concentration in the plasma is permanently raised due to various causes, such as for example ectopic ADH secretion by tumours, drug induced by administration of various psychotropic agents such as carbamazepine, neuroleptics, tricyclic antidepressants or selective serotonin reuptake inhibitors, pulmonary diseases, e.g. tuberculosis or bronchial carcinoma, or changes in the central osmoreceptors after cranial-cerebral trauma or meningitis, resulting in antidiuresis and hyponatremia and hypoosmolarity (Baylis P H 2003 *Int. J. Biochem. Cell Biol.* 35:1495-1499). Since the symptoms of the illness are originally connected with the raised AVP concentration in the plasma, the nucleic acids according to the invention can be used for the treatment and/or prevention of inadequate ADH secretion and the syndrome of inadequate ADH secretion. The effectiveness of a $V_2$ receptor antagonist in the treatment of this condition has been shown in animal studies and in SIADH patients (Saito T et al. 1997 *J. Clin. Endocrinol. Metab.* 82:1054-1057).

In a further aspect the invention relates to the use of the nucleic acids according to the invention for the production of a medicament for the treatment and/or prevention of cirrhosis of the liver and hyponatremia.

In cirrhosis of the liver a peripheral vasodilation leads to a significantly raised plasma concentration of AVP, which on account of the subsequent reduced excretion of water leads to hyponatremia and hypoosmolarility. Since the standard treatment for cirrhosis of the liver is with diuretics, which can even intensify the hyponatremia, the nucleic acids according to the invention are advantageous since, like the $V_2$ receptor antagonists, on account of the action mechanism of AVP they specifically intensify only the excretion of water and normalise an existing hypoosmolarity and hyponatremia. In patients with cirrhosis of the liver a significant increase in the urine volume and reduction of the urine osmolality was detected after a single administration of a $V_2$ receptor antagonist.

However, an increase in the AVP plasma level was found to be dose dependent, which in the case of long term medication possibly cancels out the diuretic effects of the receptor antagonist (Inoue T et al. 1998 *Clin. Pharmacol. Ther.* 63:561:570). The present inventors are currently of the opinion that the nucleic acids according to the invention used in the treatment of hyponatremia in cirrhosis of the liver do not produce any rise in the AVP plasma level, and would therefore present a significant advantage compared to the $V_2$ receptor antagonist.

In a further aspect the nucleic acids according to the invention can be used for the prevention and/or treatment of cerebral oedema. In this case, within the scope of the present invention the nucleic acids according to the invention can also be used to treat cranial-cerebral trauma or to treat strokes. It is possible within the scope of the present invention to use the nucleic acids according to the invention to treat and/or prevent cerebral oedema, where this is the result in particular of a cranial-cerebral trauma or a stroke.

In the treatment of cerebral oedema after cranial-cerebral trauma or stroke, loop diuretics such as furosemide are used as supportive treatment in the prior art. These drugs may however on account of their mode of action, which involves an increased loss of $Na^+$, $K^+$, and $Cl^-$, interfere in the electrolyte equilibrium of the body fluids and thereby lead to hyponatremia and/or hypokalemia. When using the nucleic acids according to the invention, which likewise have a diuretic effect, there is no interference in the electrolyte balance, since due to the inhibition of water reverse-resorption in the collecting tubules of the kidney, there is no ion loss but only an increased water excretion. In an animal model of cerebral oedema after cranial-cerebral trauma, the formation of the cerebral oedema could be stopped in a dose-dependent manner with a $V_2$ receptor antagonist (Lazlo F F 1999 *Eur. J. Pharmacol.* 364:115-122).

In a further aspect the invention relates to the use of the nucleic acids according to the invention for the treatment and/or prevention of a tumour. The tumour is in particular of the type that expresses one or more receptors that are selected from the group comprising $V_1$ receptors, $V_2$ receptors and $V_3$ receptors.

In tumours of the hypophysis which secrete ACTH, and also in ectopic ACTH syndrome, the $V_3$ receptor is overexpressed (De Keyser Y 1996 *J. Clin. Invest.* 97:1311-1318). Since the mitogenic action of AVP is known for a whole range of cell types (see above), but is mediated by the $V_1$ receptor, AVP is involved by stimulation via the $V_3$ receptor in the tumorigenesis of ACTH-secreting tumours. As a result of this action mechanism as well as that of the nucleic acids according to the invention, the latter can be used to inhibit tumorigenesis.

In small cell bronchial carcinoma, a subtype of bronchial carcinoma, which in the Western world is the main cause of deaths due to cancer in males and the second most common cause of death in women, all three known AVP receptors and AVP itself are expressed. The same is also true of breast cancer, which is one of the most common malignant diseases in women (North W G 1000 *Exp. Physiol.* 85:27-40). The occurrence of AVP and of all three AVP receptors in the aforementioned tumour is the basis of the thesis of the present invention, namely that AVP plays an essential role in the physiology of these tumours. Consequently, the nucleic acids according to the invention can also be used to inhibit the tumours and specifically the aforementioned tumours.

In a further aspect the present invention relates to the use of the nucleic acids according to the invention to prevent premature births.

AVP and oxytocin stimulate uterine contractions via their respective receptors in the uterus, and are decisive in initiating the birth process. Both hormones are similarly involved in premature births, which on the one hand present enormous health risks for premature babies and on the other hand place an enormous strain on the public healthcare system. However, premature births can be effectively prevented by the oxytocin analogue atosiban, which blocks the $V_1$ receptor as well as the oxytocin receptor (Akerlund M 2002 *Prog. Brain. Res.* 139: 359-365). This forms the basis for the use of the nucleic acids according to the invention in preventing premature births.

In a further aspect the present invention relates to the use of the nucleic acids according to the invention for the treatment and/or prevention of primary dysmenorrhoea.

Primary dysmenorrhoea is accompanied by colic-like hypogastric-uterine pain caused by powerful contractions of the uterus during and to some extent already before menstruation. Women who suffer from this condition have a raised AVP plasma level. Therapeutically positive effects can be achieved by the use of the synthetic oxytocin analogue atosiban and the non-peptide receptor antagonist SR 49059, both of which equally block the $V_1$ receptor and the oxytocin receptor (Akerlund M 2002 *Prog. Brain. Res.* 139:359-365).

This forms the basis of the use of the nucleic acids according to the invention for the treatment and/or prevention of primary dysmenorrhoea.

The nucleic acids according to the invention may furthermore be used as starting material for the design of pharmaceutical active substances (drug design). In principle there are two possible approaches to this. One approach consists in screening libraries of compounds, such libraries of compounds preferably being libraries of low molecular weight compounds (low or small molecules). Such libraries are known to those skilled in the art in this field. Alternatively, according to the present invention the nucleic acids may be used for the rational design of active substances.

The rational design of active substances may take as its starting point any of the nucleic acids according to the present invention, and involves a structure, in particular a three-dimensional structure, which is similar to the structure of the nucleic acid or acids according to the invention or is identical to that part of the structure of the nucleic acid or acids according to the invention which mediates the binding to vasopressin and oxytocin. In either case, such a structure still shows the same or an at least similar binding behaviour as the nucleic acid or acids according to the invention. In either a further step or as an alternative step, in the rational design of active substances the preferably three-dimensional structure of those parts of the nucleic acids binding to vasopressin or oxytocin is imitated by chemical groups, which are preferably different from nucleotides and nucleic acids. By means of this imitation, also termed mimicry, a compound can be constructed that is different from the nucleic acid or nucleic acids that was/were used as starting materials for the rational design of the active substance. Such a compound or active substance is preferably a small molecule or a peptide.

In the case of screening compound libraries using competitive tests, which are known to those skilled in this field, suitable vasopressin analogues, vasopressin agonists, vasopressin antagonists, oxytocin analogues, oxytocin agonists or oxytocin antagonists can be discovered. Such competitive assays may be constructed as follows. The nucleic acid according to the invention, preferably an spiegelmer, i.e. a L-nucleic acid binding the target molecule, is coupled to a preferably solid phase. In order to identify vasopressin analogues, vasopressin provided with a marker is added to the test system. Alternatively the vasopressin could also be coupled to a solid phase and the nucleic acid according to the invention could be labeled. A potential analogue or a potential agonist or antagonist would compete with the vasopressin molecules that bind to the spiegelmer, which would cause a reduction of the signal that is obtained from the corresponding marker. The screening for agonists or antagonists may include the use of a cell culture test system that is known to those skilled in this field. In principle the same approaches may also be employed when using oxytocin.

In a further aspect the nucleic acids according to the invention may as a result of their characteristic binding behaviour to vasopressin or oxytocin be used for target validation. The nucleic acids according to the invention may be used in an ex vivo organ model in order to study the function of vasopressin and oxytocin. In principle there exist ex vivo models in which vasopressin agonists/antagonists can be tested, e.g. isolated, perfused kidneys or isolated aorta in an organ bath.

A kit according to the present invention may include at least one or more of the nucleic acids according to the invention. In addition the kit may include at least one or more positive or negative controls. As positive controls there may be used for example vasopressin or oxytocin, against which the nucleic acid according to the invention has been screened, or to which it binds, preferably in liquid form. As negative control there may be used inter alia a peptide that behaves as regards its biophysical properties in a similar way to vasopressin and oxytocin, but which is not recognised by the nucleic acids according to the invention, or a peptide having the same amino acid composition but a different sequence to vasopressin and oxytocin.

In addition the kit may include one or more buffers. The various constituents may be present in the kit in dry or lyophilised form, or dissolved in a liquid. The kit may include one or more vessels, which in turn may contain one or more of the constituents of the kit. Preferably the vessels contain batches of reactants that are required for a single implementation of an experiment using one or more constituents of the kit.

It is also possible within the scope of the present invention to use the nucleic acids according to the invention to detect the target molecule such as vasopressin or oxytocin. For this purpose, but also in general, the nucleic acids according to the invention may be labeled directly or indirectly. Preferably the labeling is selected from the group comprising radioactive tracers, fluorescence labeling or labeling suitable for magnetic resin spectroscopy, such as for example europium.

The present invention is described in more detail hereinafter with the aid of the following figures and examples, from which further features, embodiments and advantages may be taken. In the figures:

FIG. 1 is a schematic diagram of the automated RNA selection;

FIG. 2 is a schematic diagram of the workspace of the used in vitro selection robot;

FIG. 3 shows the sequence of AVP-binding clones (SEQ ID NOS 69, 2, and 70-82, respectively, in order of appearance) and the consensus sequence (SEQ ID NO: 83) subsequent to the automated in vitro selection;

FIG. 4 shows sequences of AVP-binding clones (SEQ ID NOS 69 and 2-23, respectively, in order of appearance) and the consensus sequence (SEQ ID NO: 84) subsequent to in vitro selection;

FIG. 5 shows a comparison of the binding behaviour of the sequences CHF-15-B4 and CHF-134-A9, represented as binding to AVP in percent as a function of the nucleic acid concentration;

Figure 16:
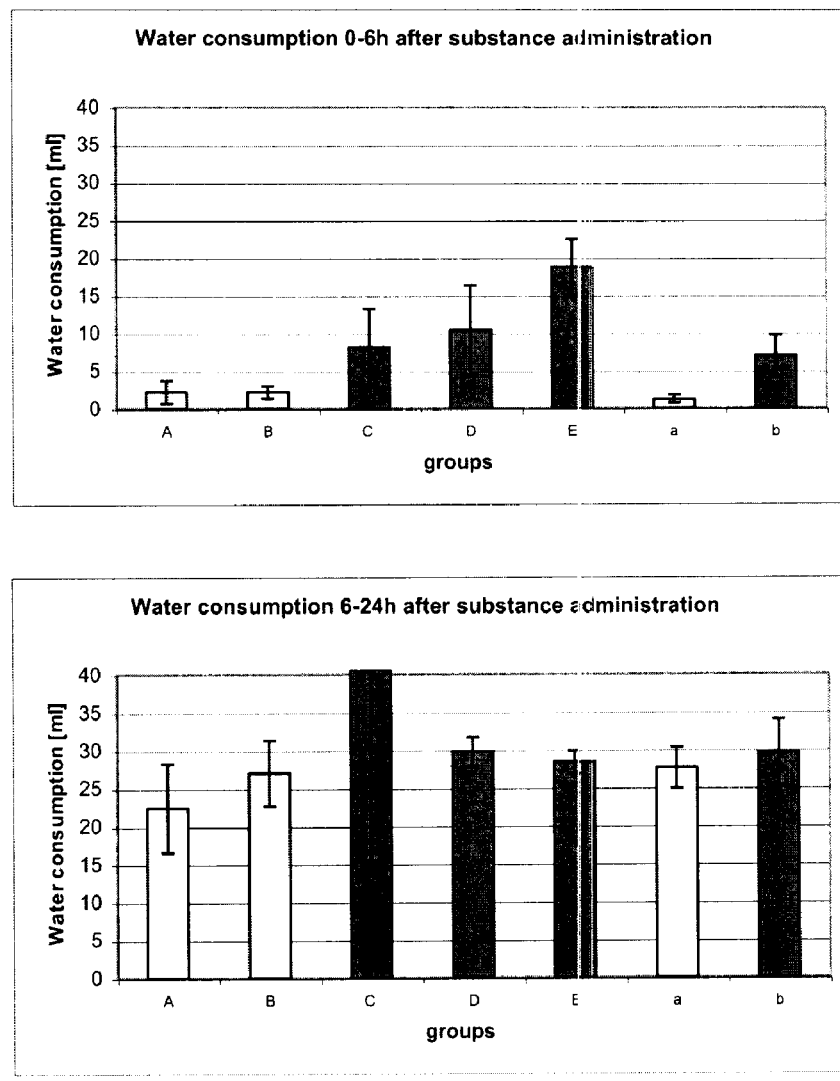

FIG. 6 shows variants of sequences (SEQ ID NOS 24, 25, 56, 26, 57, 27, 58, 28, 59, 29, 60, 30, 61, 85-88, 26, 31, 26, 32, 26, 33, 26, 34, 26, and 35, respectively, in order of appearance) after site-directed modification and truncation using internal PEG spacer moieties as well as a consensus sequence (SEQ ID NOS 89 & 90, respectively) derived therefrom, in which the variants have unaltered 5'- and 3'-ends;

FIG. 7 shows variants of sequences (SEQ ID NOS 26, 57, 26, 32, 38, 62, 39, 63, 40, 63, 41, 63, 42, 63, 43, 63, 43-45, 63, 45, 46, 64, 47, 64, 48, 49, 47, 49, 48, 49, and 47, respectively, in order of appearance) after site-directed modification and truncation using internal PEG spacer moieties as well as a consensus sequence (SEQ ID NOS 91 & 92, respectively) derived therefrom, in which the variants have altered 5'- and 3'-ends;

FIG. 8 is a representation of the secondary structure model (SEQ ID NOS 93 and 47, respectively) of the AVP-binding spiegelmer CHF-F-037;

FIG. 9 is a chromatogram of the 3'-amino-modified spiegelmer CHF-F-037-3'NH$_2$, which is obtained by means of IEX-HPLC;

FIG. 10 is a mass spectrum of the 3'-amino-modified spiegelmer CHF-F-037-3'NH$_2$, which is obtained by means of MALDI-TOF;

FIG. 11 is an electropherogram of the 3'-amino-modified spiegelmer, which is obtained by means of CGE (capillary gel electrophoresis);

FIG. 12 is a chromatogram of the spiegelmer CHF-F-037-3'PEG modified with a 40 kDa PEG, which is obtained by means of RP-HPLC;

FIG. 13 shows the inhibition of the AVP-$V_2$ receptor interaction by the spiegelmers CHF-F-037 and CHF-F-037-3'PEG, represented as the decrease in the biosynthesis of cAMP as a function of the concentration of the spiegelmer in cAMP/well on stimulation with 1 nM AVP;

FIG. 14A shows the inhibition of the AVP-$V_1$ receptor interaction by CHF-F-037, represented as the percentage decrease in the intracellular Ca release as a function of the concentration of the spiegelmer in percent of 100% release on simulation with 5 nM AVP;

FIG. 14B shows the inhibition of the AVP-$V_1$ receptor interaction by CHF-F-037-3'PEG, represented as the percentage decrease in the intracellular Ca release as a function of the concentration of the spiegelmer in percent of 100% release on simulation with 5 nM AVP;

FIG. 15 are diagrams showing the urine volume of various groups of rats after different periods of time after substance administration;

FIG. 16 are diagrams showing the water consumption of various groups of rats after different periods of time after substance administration;

FIG. 17 are diagrams showing the osmolality in the urine of various groups of rats after different periods of time after substance administration; and FIG. 18 are diagrams showing the Na content in the urine of various groups of rats after different periods of time after substance administration.

EXAMPLE 1

Automated D-AVP Selection

A. Materials

Fine Chemicals and Enzymes

NTPs and dNTPs were obtained from Larova, Berlin. The T7 RNA polymerase (50 U/μl) was obtained from Stratagene, Heidelberg; DNase I from Sigma-Aldrich, Taufkirchen; thermostable Vent exo⁻ DNA polymerase (2 U/μl) from New England Biolabs; SuperScript II reverse transcriptase (200 U/μl), as well as RNase Out RNase inhibitor (40 U/μl) from Invitrogen. The reagents for the RT-PCR in the context of the automated selection were obtained from Qiagen, Hilden.

Target Molecule Human D-AVP [D-(Arg$^8$)-Vasopressin]

The nonapeptide D-AVP (amino acid sequence: Cys-Tyr-Phe-Gln-Asn-Cys-Pro-Arg-Gly (SEQ ID NO: 1)) was synthesised by BACHEM, Heidelberg. The molecule carries a biotin group on the carboxy terminal Gly via an additionally inserted lysine so as to be able to separate bound from unbound nucleic acids by means of the biotin-streptavidine interaction with affinity chromatography materials such as NeutrAvidin agarose or Streptavidin-UltraLink (Pierce).

Nucleic Acid Libraries and Oligonucleotide Primers

The employed startpool DE5-7.34 was synthesised by NOXXON Pharma AG, and the oligonucleotide primers DE5.T7 and DE5.R used for the RT-PCR were synthesised at IBA GmbH, Göttingen, using standard phosphoramidite chemistry:

Library DE5-7.34; synthesised reverse strand
(SEQ ID NO: 65)
5'-GTGGAACCGACTCACCTGAGCG-N$_{34}$-CGCTGCTGTTGTCTAAGCTC C-3'

Forward primer DE5.T7
(SEQ ID NO: 66)
5'-TCTAATACGACTCACTATAGGAGCTTAGACAACAGCAG-3'

Reverse primer DE5.R
(SEQ ID NO: 67)
5'-GTGGAACCGACTCACCTGAG-3'

Cloning and sequencing of enriched pools were carried out to order by AGOWA, Berlin.

Production of the Startpool

For the generation of a startpool for the first selection round, 4 nmol of synthesised single-strand DNA (ssDNA; DE5-7.34 initial pool, reverse strand), corresponding in a complexity of about $2\times10^{15}$ molecules, were made up to a volume of 20×100 μl Taq polymerase buffer with a 3-fold excess of DE5.T7 primer by incubation with 400 units of Taq polymerase (5 U/μl) for 2 hours at 63° C. to form double-strand DNA (dsDNA). Starting from the resultant double-strand T7-RNA polymerase promoter, 4 nmol of dsDNA in T7 transcription buffer (80 mM HEPES pH 7.5; 22 mM MgCl$_2$; 1 mM spermidine; 10 mM dithiothreitol; 4 mM each of GTP, ATP, CTP and UTP; 120 μg/ml BSA) in a 2 ml reaction volume were transcribed into the corresponding RNA startpool. After the transcription reaction (for details see Section C—Enzymatic Reactions) the template DNA was digested with DNase I, the RNA was purified through an 8% denatured polyacrylamide gel, precipitated with alcohol, and dried.

B. Selection Steps

Denaturation and Folding of the RNA

All non-enzymatic steps of the selection, with the exception of the denaturation of the RNA before contacting with the target molecule D-AVP, were carried out in selection buffer (20 mM Tris-HCl, pH 7.4; 150 mM NaCl; 5 mM KCl; 1 mM MgCl$_2$; 1 mM CaCl$_2$; 0.1% [w/vol] Tween-20). The denaturation was carried out for 5 minutes at 95° C. in selection buffer without CaCl$_2$ and MgCl$_2$. After the denaturation the RNA was cooled on ice, MgCl$_2$ and CaCl$_2$ were added, and the mixture was incubated for a further 5-15 minutes at 37° C. In the first, manual rounds, 4-8 nmol of RNA-Pool were used, and in the subsequent automated rounds 0.2 nmol was used.

Binding and Separation of Matrix-binding RNA Species

Following the folding the RNA was first of all incubated while shaking at 37° C. for 15 minutes without peptide, with the matrix (Streptavidin-UltraLink Plus or NeutrAvidin-Agarose; both matrices from Pierce). This so-called preselection served to remove potential matrix binders. After this incubation step the unbound RNA was separated from the matrix by centrifugation, the supernatant was removed, and the matrix was washed with two column volumes of selection buffer. The supernatant and the wash fractions were combined and used for the further selection. In the automated process the matrix was removed by simply allowing it to sediment out, and only the supernatant was used further.

Selection of D-AVP-binding Ribonucleic Acids

For the binding reaction to D-AVP biotinylated D-AVP at various concentrations was added to the remaining nucleic acid species and incubated for 1-3 hours at 37° C. 10-80 μl of the biotin-binding matrix were next added to the binding batch and incubated once more while shaking for 10-15 minutes at 37° C. The matrix was then washed with selection buffer in order to remove non-binding RNA species from binding species. The wash volume used for this purpose was in the first three manual rounds twice the volume of the matrix, and in subsequent rounds was up to 135 times the solid phase volume.

Elution

During the first three, manually performed selection rounds, the bound RNA was eluted by incubating the matrix particles with bound RNA in 150 µl in 4 M guanidine-thiocyanate (Roth) twice for 15 minutes at 37° C. under denaturing conditions. This procedure was repeated again at 65° C. after removing the supernatant. The eluted RNA in the combined supernatants was extracted once with water-saturated phenol/chloroform/isoamyl alcohol (25:24:1) as well as twice with chloroform/isoamyl alcohol (24:1), precipitated for 30 minutes with 1 volume of isopropanol at −20° C., washed with 70% EtOH, and dried.

In the course of the further automated rounds the elution was achieved by heating the matrix particles in RT-PCR buffer (Qiagen) at 95° C. for 10 minutes.

C. Enzymatic Reactions

Transcription—Production of RNA for Use in the Selection

Transcriptions were carried out with 100 U T7 RNA-polymerase and 25-40 U RNase Out RNase inhibitor in T7 reaction buffer (80 mM HEPES pH 7.5; 22 mM $MgCl_2$; 1 mM spermidine; 10 mM dithiothreitol; 4 mM each of GTP, ATP, CTP and UTP; 120 µg/ml BSA; 0.8 M betaine) in a 100 µl volume. Per 100 µl reaction, 50-100 pmol RT-PCR Product (manual selection rounds) and 10-30 µl RT-PCR reaction with double-stranded DNA formed therein (automated selection rounds) were used as transcription template.

The reaction mixtures were incubated for 3-12 hours at 37° C. and DNase I was then added in order to digest the template DNA. The formed RNA was then separated either manually under denaturing conditions using an 8% polyacrylamide gel with 8 M urea, or in an automated manner by ultrafiltration with ultrafiltration units of non-built-in NTPs. Ultrafiltration-purified RNA was rinsed from the filter, and gel-purified RNA was eluted from the cut-out pieces of gel, precipitated with ethanol, dried, and taken up in water.

Reverse Transcription—Manual Rounds 1-3

The precipitated RNA was transcribed by means of reverse transcription into single-stranded DNA. At most 8 pmol per 40 µl reaction mixture were denatured with 1 µM DE5.R primer and the primer was hybridised on the RNA by cooling. 8 µl 5×RT buffer (first strand buffer, Invitrogen), 10 mM DTT, 0.5 mM dNTP, 0.8 M betaine were then added and incubated for 2 minutes at bei 48° C. Reverse transcription was then started with 5 U Superscript II reverse transcriptase and incubated for 30 minutes at 48° C.; 20 minutes at 50° C.; 10 minutes at 55° C. and 15 minutes at 70° C. in a thermocycler. The cDNA that was thereby formed served as template for the downstream PCR.

Reverse Transcription—Automated Rounds 4-16

The washed matrix particles with target molecule and RNA species bound thereon were resuspended in 120 µl of Qiagen OneStep RT-PCR buffer (primer concentration, 1 µM of each) and incubated for 10 minutes at 95° C. After allowing the reaction mixture to cool slowly first of all to 63° C. and finally to 50° C., the reaction was started by adding in each case 4 µl of enzyme mix (constituent of the OneStep RT-PCR kit from Qiagen). The temperature profile in the RT was as follows: 20 minutes 50° C.; 2 minutes 53.3° C.; 2 minutes 56.6° C.; 10 minutes 60° C.

PCR—Manual Rounds 1-3

10 µl of the RT reaction solution were used in each case as template for 3 PCRs each of 100 µl volume (10 µl 10× Vent buffer [New England Biolabs]; 1 µl 50 mM $MgSO_4$; 2 µl 10 mM dNTP-mix; 3 µl 100 µM DE5.T7 primer; 3 µl 100 µM DE5.R primer; 16 µl 5 M betaine; 2.5 µl Vent exo DNA polymerase). The amplification was carried out via a thermocyler program with the following profile: 95° C., 1 minute; 63° C., 1 minute; 72° C., 1 minute; overall 6-10 cycles. The amplification progress was checked on a native polyacrylamide gel after the reaction. The PCR reaction was then precipitated with alcohol, and the pellet was washed with 70% ethanol and dried. The DNA was dissolved in $H_2O$ and 50-100 pmol thereof was used as transcription template for the next selection round.

PCR—Automated Round 4-16

The PCR was started by incubating the OneStep RT-PCR batches for 15 minutes at 95° C. This was followed by 7-16 thermocycles (95° C., 30 sec; 63° C., 30 sec; 72° C., 30 sec).

During the automated rounds the course of the PCR was monitored by fluorescence measurement of aliquots from the PCR reaction, and the PCR was discontinued after the necessary threshold value had been reached (see Section D, Monitoring the PCR progress in the automated selection).

D. Monitoring the PCR Progress Within the Automated Selection

The increase in double-stranded DNA during the PCR was followed semi-quantitatively. This served for the purpose of keeping the number of PCR cycles as small as possible. In this way only as many PCR cycles are carried out as are necessary to obtain sufficient templates for the T7 reaction. During the PCR aliquots were therefore removed from the PCR batches after a certain number of cycles and added to 90 µl of a PicoGreen solution (diluted 1:400 in TE [10 mM Tris-HCl, pH 8; 1 mM EDTA]). PicoGreen is a fluorescent dye which when free in solution hardly fluoresces, but when bound to double-stranded DNA fluoresces strongly (Ex: 485 nm; Em: 520 nm). Measurement of the fluorescence compared to a non-cycled control without thermostable polymerase allows an extremely accurate estimate of the PCR progress to be obtained. After the threshold value has been reached (cycled fluorescence/uncycled fluorescence>2) an aliquot of the RT-PCR reaction can serve as template for the in vitro transcription.

E. Automated Manipulations

Starting from the third round, all manipulations apart from incorrectly performed gel purification steps were carried out in a fully automated manner on a pipetting robot. The arrangement of the individual modules used for this purpose on the workspace of the robot is shown in FIG. 2. The following modules were employed:

Fluorescence reader for checking the amplification progress during the PCR. Samples in which DNA has already been sufficiently generated are temporarily stored in a fully automated manner and do not undergo further thermocycles Double vacuum chamber with chamber A for the separation of RNA species bound to the matrix and unbound RNA species, and chamber B for the purification of transcription reactions before the start of the respective next round Holders for pipette tips Thermocycler for carrying out the PCR program as well as for various incubation steps Shaker for suspending the matrix in the binding buffer or reaction buffer 50° C. workstation, so as to be able to start enzymatic reactions directly at this temperature (hot start) and to allow PCR reactions not to cool too quickly during the sampling for the fluorescence control 4° C. workstation for temporary storage of PCR and transcription reactions 4° C. reagent stands for storing heat-sensitive reagents such as enzymes or prepared reaction mixtures RT/37° C. reagent stands for storing wash buffer RT/37° C. workstation for carrying out most manipulations Fluorescence plate workstation for preparing the samples for the fluorescence measurement Hotel for storing plates that are not currently being processed Disposal point for used pipette tips The involvement of the individual modules in the selection process described in the context of this example as well as the order of their use is shown in FIG. 1.

F. Results

Selection Procedure

In each selection round starting from round 4 three differently stringent batches as well as an empty column without D-AVP were operated as target molecules. The stringency was raised by varying the amount of wash volume used and also by employing lower D-AVP concentrations.

Rounds 1 to 3 were carried out manually, since the large amounts of matrix that are necessary for the binding of the D-AVP in the (necessarily high) concentrations of these initial rounds can no longer be reliably processed by automated pipetting devices. Starting from round 4 the selection procedure was fully automated.

In general the selected RNA of the strand with the highest stringency, i.e. the lowest peptide concentration and the largest wash volume, which in the amplification still produced a significant signal above the zero control, was used in the next round. The number of cycles that was necessary in order to reach the threshold value was used as a measure of this signal (see "Monitoring of the PCR progress"). Overall 16 selection rounds were carried out.

The populations of dsDNA molecules from round 14 (D-AVP concentration: 30 nM) and from round 16 (D-AVP concentration: 10 nM) were cloned, and a total of 48 clones were sequenced, which after alignment of the sequences could be grouped into several families. The family of molecules with the best binding properties is shown in FIG. 3. All clones of this family have the general consensus sequence shown underneath the sequence alignment in FIG. 3, with the following elements. Firstly, two complementary regions (Helix1 and Helix2) at the 5'-end and at the 3'-end, which form a seven base pair long double-stranded helix; secondly, a five nucleotide long stretch (Box1) of the sequence GUGGW; thirdly, a seven to nine nucleotide long A-rich and U-rich W stretch in which C never occurs and one G at most occurs per stretch; and fourthly a 21 nucleotide long stretch (Box2) of the sequence GGGGUAGGGMUUGGAWGGGWA (SEQ ID NO: 68). The main characteristic features of Box2 are four strictly conserved Gs, occurring twice to four times. All illustrated molecules bind to AVP and the best binder is the molecule CHF-134-A9. In addition to the AVP-binding molecule illustrated in FIG. 3, further molecules were enriched with completely different sequences during the automated selection (not shown). These molecules have significantly worse binding properties.

EXAMPLE 2

Screening of D-AVP-binding Aptamers Following the Automated Selection, By Manual, Mutagenic High Stringency Selection A. Materials Fine Chemicals and Enzymes See Example 1

Target Molecule Human D-AVP [D-(Arg$^8$)-vasopressin]

The nonapeptide D-AVP (amino acid sequence: Cys-Tyr-Phe-Gln-Asn-Cys-Pro-Arg-Gly, SEQ. ID. No.: 1) was synthesised in two variants by BACHEM, Heidelberg. Both variants carry a biotin group on the carboxy terminus in order to be able to separate the nucleic acids bound to the peptide from the unbound nucleic acids, by means of the biotin-avidin or streptavidin interaction with the affinity chromatography matrices NeutrAvidin-Agarose (NAag) and Streptavidin-UltraLink:+(SAul+), both from Pierce. The biotin is bound to the carboxy-terminal Gly via an additionally inserted lysine and for both variants different linkers are bound to the peptide part. A hydrophilic PEG bridge, consisting of amino-ethoxy-ethoxy-acetylamino-ethoxy-ethoxy-acetyl (AEEA-AEEA linker), leads to the biotinylated D-AVP(C-Lys). The more hydrophobic ε-aminohexyl-ε-aminohexyl bridge leads to the biotinylated D-AVP(C-LC-LC).

The reason for the choice of the different target molecule variants was the fact that the physicochemical properties in small peptides such as AVP are altered to a relatively greater extent by modification with chemical moieties such as biotin, than is the case with large molecules. The deviation from the natural target molecule may in the course of the selection lead to undesirable aptamers, which require the linker for high affinity binding. Accordingly, in the high stringency selection the procedure was carried out with the two different AVP derivatives in constant alternation and in alternating composition with the two avidin matrices mentioned above, in order to avoid the enrichment of molecules that require the linker region for the binding to the peptide and prevent the enrichment of the desired molecules which bind in a high affinity manner only to the pure peptide.

Nucleic Acid Libraries and Oligonucleotide Primers see Example 1

Startpool

The manual, mutagenic high stringency selection was started with double-stranded pool DNA from round 16 of the automated selection. For this purpose 10 pmol of pool DNA from round 16 were amplified by mutagenic PCR with Vent exo⁻ thermostable DNA polymerase, and transcribed in vitro with T7 RNA polymerase. The RNA was purified under denaturing conditions via an 8% polyacrylamide gel with 8 M urea, eluted, precipitated with alcohol, and taken up in water for the selection (for details see enzymatic reactions).

B. Selection Steps

Denaturation and Folding of the RNA; Used Amount of RNA see Example 1. At the start of the selection with mutagenic amplification 500 pmol of mutagenised pool RNA were used in round 17. Over the course of the selection increasingly less RNA was used with increasing stringency (5 pmol in round 29)

Binding and Separation of Matrix-binding RNA Species

See Example 1

Selection of D-A VP-binding Ribonucleic Acids

For the binding reaction to D-AVP various concentrations of biotinylated D-AVP, which became increasingly less over the course of the selection, were added to the remaining RNA species and incubated for 30 minutes at 37° C. Following this, depending on the amount of peptide used and the matrix employed, 3-20 μl of matrix were added to the binding batch and incubated once more while shaking for 10-15 minutes at 37° C. The matrix was then washed with selection buffer in order to remove non-binding RNA species from binding species. The wash volume used for this purpose was between 50 and 200 times the matrix volume.

Elution see Example 1. The elution was carried out as in the first three, manually performed selection rounds of the automated selection.

C. Enzymatic Reactions

Transcription—Production of RNA for Use in the Selection see Example 1. The generated RNA was prepared exclusively manually under denaturing conditions by gel electrophoresis.

Reverse Transcription see Example 1; Reverse transcription—manual rounds 1-3

PCR—non-mutagenic

The reversibly transcribed RNA was first of all systematically amplified under non-mutagenic conditions (see Example 1; PCR—manual rounds 1-3), in order then either to be transcribed directly in vitro or to be amplified beforehand under mutagenic PCR conditions.

PCR—mutagenic

The DNA was amplified using a two-stage PCR protocol under reaction conditions in which thermostable DNA polymerases have a high failure rate, and mutate the DNA. (Fromant et al. 1995 *Anal. Biochem.* 224:347-353). 1 pmol of the DNA amplified under standard conditions was amplified in 100 μl reaction volume (10 mM Tris, pH 8.7; 50 mM KCl; 5 μg/ml BSA; 4.82 mM $MgCl_2$; 0.8 M betaine; 0.5 mM $Mncl_2$; 3.85 mM dTTP; 0.55 mM dGTP; 0.12 mM dATP; 0.1 mM dCTP; 2 μM DE5.R primer; 2 μM DE5.T7 primer) with 8 U Taq DNA polymerase until saturation was reached, with the following temperature profile: 95° C., 1 min; 63° C., 1 min; 72° C., 3 min; overall 10-16 cycles. The amplification progress was checked after the reaction on a native 8% polyacrylamide gel. 1 pmol of the DNA amplified under mutagenic conditions was reamplified under the conditions mentioned above. The DNA was precipitated with alcohol after the second mutagenic PCR amplification and transcribed in vitro.

D. Selection Procedure

The manual high stringency selection with mutagenic PCR was carried out for 13 rounds (rounds 17-29 in the context of the automated selection). The parameters for this are shown in Table 1.

TABLE 1

| Round | Avidin matrix | D-AVP (C-Lys) | D-AVP (C-LC-LC) | RNA pool mutated | RNA pool not mutated | Signal/control ratio |
|---|---|---|---|---|---|---|
| 17 | NAag |  | 5 nM | 10 nM |  | 38 |
| 18 | NAag | 5 nM |  | 10 nM |  | 45 |
| 19 | SAul+ | 1 nM |  | 10 nM |  | 25 |
| 20 | SAul+ |  | 200 pM | 10 nM |  | 3 |
| 21 | NAag |  | 40 pM |  | 10 nM | 10 |
| 22 | NAag | 20 pM |  | 10 nM |  | 18 |
| 23 | SAul+ | 5 pM |  |  | 4 nM | 1.8 |
| 24 | SAul+ |  | 4 pM | 2 nM |  | 1.3 |
| 25 | NAag |  | 1 pM |  | 2 nM | Larger than 1 |
| 26 | NAag | 1 pM |  |  | 100 pM | Larger than 1 |
| 27 | NAag |  | 1 pM | 100 pM |  | Larger than 1 |
| 28 | SAul+ |  | 0.4 pM |  | 100 pM | Larger than 1 |
| 29 | NAag | 0.4 pM |  |  | 333 pM | Larger than 1 |

In this connection, in the course of the selection the peptide concentration as high stringency parameter was reduced to 0.4 pM. The RNA was used in excess, in order to select only the best molecules by competition among the binders. In each round depletion factors of greater than 10,000 were achieved by the chosen selection parameters and by the wash procedure (the matrix was washed with 50 to 200 times the fixed bed volume after the immobilisation of the peptide-RNA complex).

The aim of the high stringency selection was to generate, from the D-AVP-binding RNA pool existing after 16 rounds of automated selection, further optimised binders by mutation and selection. In general, in each round binding reactions were carried out with different peptide concentrations (signal) and, in comparison thereto, one reaction was carried out completely without peptide (control). The reaction which at the lowest peptide concentration still exhibited a signal/control ratio of greater than 1 was adopted in the following selection round. The table shows only the parameters of these binding reactions.

The DNA was mutagenised in each of the first four selection rounds, in order to generate as much variability as possible in the binding pool. In the following rounds the DNA was alternately non-mutagenically and mutagenically amplified so as to enrich in each case improved binders before further mutagenesis. The last three rounds were carried out without further mutagenesis. After the $29^{th}$ round the DNA was cloned and the sequence of 24 clones was determined.

Sequences

The result of the sequence analysis without the constant regions of both primers that are functionally not necessary for the binding is shown as an alignment in FIG. 4. Of the 24 clones, the length of which excluding the flanking regions is between 46 and 49 nt, three are completely identical. All the others have a very high sequence homology, which they possess being members of the family of the best binders after the automated selection. The remaining families which still existed after the automated selection have disappeared under the selection conditions of the mutagenic high stringency selection. All selected molecules have the typical consensus sequence already illustrated in FIG. 3, with the four elements Helix1 and Helix2 at the 5'-end and 3'-end, Box1, A-rich and U-rich W stretch, and Box2. Under the high stringency selection conditions the four elements have altered as follows. Helix1 and Helix2 comprise altered and different but still complementary sequences. The fifth position of Box1 is only U instead of W as before (i.e. no more A). In the A-rich and U-rich W stretch the occurrence of at most one G per stretch is reduced. After the automated selection 9 out of 15 clones, i.e. 60%, still contain one G per stretch, whereas after the high stringency selection only 6 out of 24 clones, i.e. 25%, contain one G per stretch. In Box2, where after the automated selection one W occurred at two positions, after the high stringency selection an A was no longer present in any molecule at these positions, but instead, in addition to U a C is present in some molecules at these positions. Since overall there is never a G at these positions, in the consensus sequence an H is located at both these positions. Thus, the consensus sequence shown in FIG. 4 for a L-(Arg8)-vasopressin-binding L-RNA is obtained from the sequence analysis of the clones from round 29 after the manual high stringency selection and from round 16 after the automated selection.

Ranking

The clones were tested as regards their binding to AVP. All clones exhibited binding to the peptide. The clone CHF-157-B4 exhibited on comparison the best binding. In a competition test CHF-157-B4 was measured compared to the best clone (CHF-A9) from the 16th round after automated selection. In this test the dissociation constant of CHF 157-B4 for the binding to biotinylated AVP was 9.5 nM, whereas for CHF-134-A9 it was 120 nM, as is also shown in FIG. 5. Due to the mutagenic high stringency selection the quality of the binding was improved by a factor of roughly 12.

EXAMPLE 3

Development and Truncation of AVP-binding Aptamers By Incorporation of Internal PEG Spacer Moieties Methodology After the two-stage selection process (automated selection and manual, mutagenic high stringency selection) variants were specifically constructed and chemically synthesised on the basis of the best binder, in which nucleoside positions were internally replaced by incorporating a PEG spacer moiety or PEG group (hexaethylene glycol). In this way the molecule was to be truncated and its binding properties were to be further optimised. The aptamer CHF-157-B4 (called CHF-F-000 for the further development) had proved to be the best binder of all selected molecules. Starting from this 47 nt-long aptamer, the synthesised variants were compared with one another and with the starting molecule in a competitive ranking assay, and the best, truncated molecule was synthesised as spiegelmer, i.e. as L-nucleic acid.

Synthesis of the PEG Spacer Variants

The constructed and tested variants were synthesised by NOXXON Pharma AG by standard phosphoramidite chemistry using hexaethylene glycol phosphoramidite and, after deprotection, were purified by preparative, denaturing gel electrophoresis (12% PAA, 8 M urea, tris-borate-EDTA buffer) and then electroeluted.

Competitive Ranking Assay

The test is based on the competition of the AVP binding of a radioactively labeled aptamer by non-labeled aptamers. In this, the strength of the competition of the labeled aptamer by itself (unlabelled) serves as reference, against which the quality of the variants are measured. The molecule which on comparison competes most strongly and better than the reference is used as new reference when analysing further variants.

The reference aptamer was labeled by T4 polynucleotide kinase (Invitrogen) at the 5'-end with [$\gamma$-$^{32}$P] (400 ATP Ci/mmol; Hartmann Analytic, Brunswick) to a specific radioactivity of 60,000-120,000 cpm/pmol. 0.2 nM of the aptamer was then incubated with biotinylated D-AVP (0.5 nM) together with unlabelled aptamers in excess or without unlabelled aptamers as control for one hour in selection buffer. After immobilisation on 1 µl SAul+matrix, removal of the supernatant and washing the matrix with 50-100 µl selection buffer the binding reactions were measured in a scintillation counter (Beckman, USA).

PEG Spacer Variants of the AVP-binding Aptamer CHF-F-000

On the basis of the sequence analysis of all clones from round 16 after the automated selection and round 29 after the following high stringency selection, the adenosine/uridine-rich W stretch between Box1 and Box2 turned out to be the region in which the replacement of nucleosides by the internal PEG spacer appeared to be most likely, in order to truncate the molecule without however affecting its functionality. FIG. 6 shows the tested variants, in which the 5'-end and 3'-end remain unaltered. The variants CHF-F-008 and CHF-F-009, in contrast to all the other tested variants, did not show any binding at all, since here the PEG spacer lies in the Box2, which is obviously essential for the molecule. The 44 nucleotide-long variant CHF-F-003 proved to be best, which although internally truncated by three nucleosides binds just as well as the 47 nucleotide-long starting molecule CHF-F-000 to AVP.

Apart from the variants with unaltered molecule ends, a number of variants were also tested in which the 5'-end and the 3'-end were placed in the adenosine/uradine-rich W stretch and the PEG spacer was displaced to the base of the helix, as illustrated in FIG. 7. The now open adenosine/uracil-rich W stretch was successively truncated and in parallel to this the helix was truncated by the outermost base pair. Of the tested molecules which all still bind to AVP, CHF-F-033 (40 nt) and CHF-F-037 (38 nt) prove to be best. They bind just as well as the reference molecules CHF-F-003 and CHF-F-000. The four variants in which the U had been removed at the 3'-end of Box1 bind significantly worse, which underlines the importance of this Box1 and shows that, for a full functionality, this stretch must consist of GUGGU. In contrast to this, the U of the 3'-end of the A-rich and U-rich stretch (see CHF-F-033 and CHF-F-037) can be removed without the function thereby being affected. Since CHF-F-037, whose secondary structure model is shown in FIG. 8 is, with 38 nucleotides, the shortest of the tested molecules without any loss of binding quality, it was produced as spiegelmer, and was analysed biophysically and in the context of cell culture tests in order ultimately to demonstrate the effectiveness in animal tests.

EXAMPLE 4

Chemical Synthesis and Preparation of the 3'-terminally PEGylated Spiegelmer CHF-F-037-3'PEG The spiegelmer was coupled at the 3'-end covalently to 40 kDa large polyethylene glycol (PEG), in order to slow down the excretion of the spiegelmer by the kidneys after application in animal studies. With the thereby enlarged spiegelmer a significantly longer residence time is achieved and thus a prolonged effectiveness of the thereby enlarged spiegelmer in the plasma.

Chemical Solid Phase Synthesis

The spiegelmer was prepared by solid phase synthesis in an ÄktaPilot100 Synthesiser, Amersham Biosciences (General Electric Healthcare, Freiburg), via 2' TBDMS RNA phosphoramidite chemistry (M. J. Damha, K. K. Ogilvie, Methods in Molecular Biology, Vol. 20 Protocols for oligonucleotides and analogues, ed. S. Agrawal, p. 81-114, Humana Press Inc. 1993). L-rA(N-Bz)-, L-rC(Ac)-, L-rG(N-ibu)-, L-rU- and hexaethylen glycol phosphoramidite were obtained from ChemGenes Corp., Wilmington, Mass. (USA). The synthesis was carried out on 3'-amino-modified C-6 CPG with a pore size of 1000 Å, ChemGenes Corp., Wilmington, Mass.

(USA). A 0.3M solution of benzylthiotetrazole, CMS-Chemicals, Abingdon (UK) in acetonitrile, 3.5 eq. of the corresponding 0.1M amidite solution in acetonitrile, was used for the coupling with a coupling time of 15 minutes. An oxidation capping cycle was employed. Further standard solvents and reagents that are used in oligonucleotide synthesis were obtained from Biosolve (Valkenswaard, NL). The spiegelmers were synthesised (DMT-ON) and, after deprotection, were purified by means of preparative RP-HPLC (Wincott F et al 1995 Nucleic Acids Res. 23: 2677) using Source 15RPC Medium, Amersham Biosciences. The 5'DMT group was removed with 80% acetic acid (30 minutes, RT). After adding aqueous 2M NaOAc solution the spiegelmer was desalted by tangential flow filtration with a 5K regenerated cellulose membrane, Millipore Corp. Bedford, Mass. (USA). The yield of purified 3'-amino-modified spiegelmer was in the range 60-75 OD/µmol. The IEX-HPLC, MALDI-TOF and CGE analysis of the purified spiegelmer is shown in FIGS. 9, 10 and 11.

PEGylation

For the PEGylation (cf. European Patent Application EP 1 306 382) the purified 3'-amino-modified spiegelmer (18 µmol) was dissolved in a mixture of water (2.5 ml), DMF (5 ml) and 5 ml of buffer A. Preparation of buffer A: water was added to a mixture of citric acid monohydrate (7.00 g), boric acid (3.54 g), phosphoric acid (2.26 ml) and 1M sodium hydroxide (343 ml), to produce 1 litre of the stock solution. This stock solution was adjusted to pH 8.4 by adding 1M hydrochloric acid.

The pH value of the spiegelmer solution was adjusted to 8.5 by adding 1M sodium hydroxide. 40 kDa PEG-NHS ester (Nektar Therapeutics, Huntsville, Ala. (USA)) was added in portions of 0.6 equivalent/30 minutes at 37° C. until a maximum conversion of 75-85% was achieved at 2.4 equivalents. During the addition of PEG-NHS ester the pH of the reaction mixture was maintained at a value between 8.0 and 8.5 by adding 1M sodium hydroxide.

The PEGylated spiegelmer was purified by means of RP-HPLC through Source 15RPC Medium, Amersham Biosciences, and a 0.1M triethylammonium acetate gradient in water (buffer B) and acetonitrile (buffer C). Before injection into the HPLC column, 8M urea (4 ml), buffer A (4 ml) and buffer B (4 ml) were added to the reaction mixture and heated for 15 minutes at 95° C. Excess PEG was eluted at 5% buffer. PEGylated spiegelmer eluted at 10-15% buffer C. Product fractions with an HPLC purity >95% were combined and 2 M NaOAc (40 ml) was added. After desalting by tangential flow filtration with a 5K regenerated cellulose membrane, Millipore Corp. Bedford, Mass. (USA), the purified PEGylated spiegelmer was obtained in a yield of 35-50%. 390 mg of PEGylated spiegelmer were obtained, starting from 240 mg of 3'-amino-modified spiegelmer. The IEX-HPLC analysis of the purified 40 kDa PEGylated spiegelmer CHF-F-037-3'PEG is shown in FIG. 12.

EXAMPLE 5

Biophysical Characterisation of the Spiegelmer CHF-F-037 By Isothermal Calorimetry (ITC)

Methodology

Calorimetric measurements for the determination of dissociation constants were carried out with a VP-ITC microcalorimeter (MicroCal, Northampton, Mass.). The spiegelmer and ligand solution to be measured was degassed under a vacuum in measurement buffer (20 mM Tris-HCl, pH 7.4; 150 mM NaCl; 5 mM KCl; 1 mM $MgCl_2$; 1 mM $CaCl_2$) at 37° C. The spiegelmer was added in an amount of 2-6 µM to the measurement cell of the instrument (cell volume: 1.43 ml), and 25 µM of the ligand was drawn into the injection syringe (syringe volume: 0.25 ml). The ligand solution was, after an initial 3 µl injection, injected into the measurement cell in 7.5 µl aliquots over a time of in each case 6 seconds. The measurement temperature was 37° C. and the time between two consecutive injections was in each case 5 minutes.

Results

The results of the measurements of non-PEGylated spiegelmer CHF-F-037 and PEGylated spiegelmer CHF-F-037-3'PEG against L-AVP as well as of CHF-F-037-3'PEG against oxytocin are summarised in Table 2.

TABLE 2

| Measurement | Spiegelmer | Peptide | $K_d$ | Activity |
|---|---|---|---|---|
| 1 [110] | CHF-F-037 | L-AVP | 1.7 nM | 46.8% |
| 2 [120] | CHF-F-037-3'PEG | L-AVP | 1.3 nM | 59.1% |
| 3 [193] | CHF-F-037-3'PEG | L-oxytocin | 16 nM | 69.8% |

The dissociation constant for the spiegelmer in both the PEGylated and non-PEGylated form is 1.5 nM. Accordingly, the spiegelmer binds with a very high affinity to AVP, which means that it can be used in the treatment of medical conditions in which AVP is implicated. The similar substance oxytocin is bound with a roughly ten times lesser affinity. However, this affinity too is sufficient to be able to achieve satisfactory results with the spiegelmer in medical conditions involving oxytocin. The dissociation constant of 1.5 nM for the AVP-binding spiegelmer is about 600 times better compared to the dissociation constant of the DNA spiegelmer already known in the prior art (Williams KP et al. 1997 Proc. Natl. Acad. Sci USA 94: 11285-11290).

EXAMPLE 6

Biological Characterisation of the Spiegelmer CHF-F-037 in Cell Culture

A. Methodology

Analysis of the Inhibition of the Binding of $(Arg^8)$-vasopressin to the $V_2$ Receptor By $(Arg^8)$-vasopressin-binding Spiegelmers The basis of this method is the inhibition of the AVP-$V_2$ receptor interaction and the subsequent formation of cAMP. Cells of the porcine kidney epithelial cell line LLC-PK1 (ATCC-CL-101), which express the renal $V_2$ receptor, were seeded out in an amount of $6 \times 10^4$ per well in a 96-well microtitre plate and cultured overnight at 37° C. and 5% $CO_2$ in medium 199 (Invitrogen, Karlsruhe), which additionally contains 10% of heat-inactivated foetal calf serum (FCS), 4 mM L-alanyl-L-glutamine (GLUTAMAX), 50 units/ml penicillin, 50 µg/ml streptomycin.

The spiegelmers were incubated together with 1 nM L-AVP (Calbiochem) in Hank's balanced salt solution (HBSS)+1 mg/ml BSA for 15-60 minutes at RT or 37° C. in a 0.2 ml low profile 96-tube plate. 2 µl of 50 mM 3-isobutyl-1-methylxanthine (IBMX solution from Calbiochem) were added shortly before the addition of the binding batches to the cells. The cells were pretreated with 1 mM IBMX 20 minutes before the addition of the AVP/spiegelmer batches.

To effect stimulation the medium was aspirated from the cells and the pre-incubated binding batches were added. After incubation for 30 minutes at 37° C. the cell supernatants were aspirated and the cells were lysed with 50 µl/well of lysis buffer for 30 minutes at 37° C. The lysis buffer is a constituent of the "cAMP-Screen™ System" kits (Applied Biosystems, Darmstadt), with which the cAMP content of the extracts is measured. 10 µl of the extracts were used in each case in the test. The test was carried out according to the manufacturer's instructions:

In an assay plate (coated with goat anti-rabbit IgG) 10 µl/well of the lysate were added to 50 µl of the lysis buffer and mixed with 30 µl/well of the cAMP-alkaline phosphatase conjugate diluted according to the manufacturer's instructions. Following this 60 µl/well of the cAMP antibody supplied with the kit were added. Incubation was carried out for 1 hour at RT while shaking. Following this the solutions were removed from the wells and these were washed six times with the supplied wash buffer. For the detection, 100 µl/well of CSPD/Sapphire-II RTU substrate were added, incubated for 30 minutes at RT, and the luminescence was measured in a POLARstar Galaxy multidetection plate reading instrument (BMG LABTECH, Offenburg).

Analysis of the Inhibition of the Binding of (Arg$^8$)-vasopressin to the $V_1$ Receptor By (Arg$^8$)-vasopressin-binding Spiegelmers The basis of this method is the inhibition of the AVP-$V_1$ receptor interaction and the subsequent intracellular release of calcium. Cells of the line A7r5 (from smooth muscle cells of rat aorta, ATCC-CRL-144), which express the vascular $V_1$ receptor, were seeded out in an amount of $4 \times 10^4$ per well in a black 96-well microtitre plate with a clear base (Greiner Bio-One, Frickenhausen) and cultured overnight at 37° C. and 5% $CO_2$ in DMEM, which additionally contained 10% foetal calf serum, 4 mM L-alanyl-L-glutamine (GLUTAMAX), 50 units/ml Penicillin and 50 µg/ml Streptomycin.

The spiegelmers were incubated together with 5 nM L-AVP (Calbiochem, Schwalbach) in Hanks balanced salt solution (HBSS) in a 0.2 ml low profile 96-tube plate for 15-60 minutes at RT or 37° C. HBSS was supplemented with 1 µg/ml BSA, 5 mM probenicide and 20 mM HEPES (HBSS+).

Before the addition of the calcium indicator dye Fluo-4, the cells were each washed once with 200 µl HBSS+. 50 µl of the indicator buffer solution (10 µM Fluo-4 (Molecular Probes, Eugene, Oreg.), 0.08% Pluronic 127 (Molecular Probes) in HBSS+) were then added and incubated for 60 minutes at 37° C. Following this the cells were washed three times with 180 µl HBSS+ each time. 90 µl of HBSS+ were then added per well.

The measurement of the fluorescence signals was carried out at an excitation wavelength of 485 nm and at an emission wavelength of 520 nm in a POLARstar Galaxy multidetection plate reading instrument (BMG LABTECH).

For the parallel measurement of several samples the wells of a (vertical) row of a 96-well plate were in each case measured jointly. For this, three measurement values for setting the base line were first of all recorded at 4-second intervals. The measurement was then interrupted, the plate was removed from the reading instrument 10 µl of the stimulation solution from the low profile 96-tube plate in which the pre-incubation was carried out were added with a multi-channel pipette, to the wells of the row to be measured. The plate was then reinserted into the reading instrument and the measurement was continued (a total of 20 measurements at 4-second intervals).

From the obtained measurement curves the difference between the maximum fluorescence signal and the fluorescence signal before the stimulation was determined for each individual well and was plotted against the concentration of spiegelmer.

B. Results

Inhibition of the AVP-$V_2$ Receptor Interaction

The inhibition of the interaction of AVP with the $V_2$ receptor on LLC-PK1 cells by the PEGylated and the non-PEGylated spiegelmer CHF-F-037 is shown in FIG. 13. The amount of cAMP formed is plotted against the concentration of spiegelmer. The graphical evaluation gives as concentration of spiegelmer at which only 50% of the cAMP amount present in the control is formed, an IC50 of approx. 1 nM in both cases. Thus, an improvement by a factor of about 3000 is obtained compared to the efficiency of the AVP-binding DNA spiegelmer already known from the prior art (Williams K P et al. 1997 *Proc. Natl. Acad. Sci USA* 94: 11285-11290), for which in the same test an IC50 of approx. 3 µM had been found.

Inhibition of the AVP-$V_1$ Receptor Interaction

The inhibition of the interaction of AVP with the $V_1$ receptor on A7r5 cells by the PEGylated and the non-PEGylated spiegelmer CHF-F-037 is shown in FIG. 14. A7r5 cells were stimulated with 5 nM AVP or with AVP that had been pre-incubated together with different concentrations of spiegelmer at 37° C., and the thereby induced intracellular release of calcium was measured. The figure shows the percentage decrease in the signal as a function of increasing concentrations of spiegelmer. The signal was set at 100%, which was measured in the absence of spiegelmer (% of the control). The non-PEGylated spiegelmer inhibits the AVP-induced, intracellular release of calcium with a half-maximum effective concentration (IC50) of approx. 6 nM. The PEGylated spiegelmer inhibits with an IC50 value of approx. 7 nM.

EXAMPLE 7

Study of Diuresis in Rats After Administration of the Spiegelmer CHF-F-037

A. Experimental Protocol

In order to test in vivo the effect of the spiegelmer CHF-F-037 and its variant CHF-F-037-3'PEG provided with a 40 kDa PEG residue, a diuresis study was carried out with male Sprage-Dawley rats (Elevage Janvier, Le Genest St. Isle, France) of 239-290 g body weight at aurigon GmbH (Tutzing).

The experimental protocol comprised seven different groups each containing five animals, which were to receive intravenously or intraperitoneally different concentrations of PEGylated and non-PEGylated spiegelmer as well as inactive control spiegelmer and pure buffer solution (vehicle) as controls, as illustrated in Table 3.

| Group | Group size | Substance | Dose [mg/kg] | Dose [nmol/kg] | Volume [ml/kg] | Administration |
|---|---|---|---|---|---|---|
| A | 5 | PBS (pH 7.4) | — | — | 2 | i.v. |
| B | 5 | Control SPM-5'PEG | 105.9 | 2000 | 2 | i.v |
| C | 5 | CHF-F-037-3'-PEG | 4.2 | 80 | 2 | i.v |
| D | 5 | CHF-F-037-3'-PEG | 21.2 | 400 | 2 | i.v |
| E | 5 | CHF-F-037-3'-PEG | 106 | 2000 | 2 | i.v. |
| A | 5 | Control SPM | 25.5 | 2000 | 2 | i.p. |
| B | 5 | CHF-F-037 | 25.9 | 2000 | 2 | i.p. |

Before the actual experiment the total number of 35 animals were acclimatised on day −5 (before the start of the study) to the laboratory conditions and on day −2 were placed individually in metabolic cages at 22±3° C. and 30-70% atmospheric humidity. The animals had free unlimited access at all times to sterile water and dry food (R/M standard diet, autoclaved; Ssniff Spezialdiaten GmbH, Soest). On day −1 the water consumption over the period 0-6 h and 6-24 h, and the urine volume over the period 0-2 h, 2-4 h, 4-6 h and 6-24 h, was measured in one animal from each group.

On day 0 the substances were administered to the animals of groups A to E intravenously (i.v.) into the tail vein as a bolus in a volume of 2 ml/kg body weight. The substances were injected intraperitoneally (i.p.) in a volume of 2 ml/kg body weight into the animals of groups a and b. All animals were weighed directly before the injection and the corresponding injection volume was calculated. After the administration of the test substances (day 0) the water consumption for all animals was measured over the period 0-6 h and 6-24 h and the urine volume was measured over the period 0-2 h, 2-4 h, 4-6 h and 6-24 h. The collected urine was stored at 2-8° C. and its osmolality and sodium content were likewise measured over the period 0-2 h, 2-4 h, 4-6 h and 6-24 h. This experimental design was checked and approved by the local regulatory authorities; Registration No. 209.1/211-2531.2-14/02.

B. Results

Diuresis and Water Consumption

Intravenously administered CHF-F-037-3'PEG exhibited a dose-dependent increase in the urine volume for the groups C, D and E, compared to the groups A (only vehicle) and B (inactive spiegelmer in an amount of 2000 nmol/kg), as is shown in FIG. 15. The effect continued for the period 0-2 h after the administration and, for the higher dosed groups (400 and 2000 nmol/kg) also persisted over the following periods (2-4 h and 4-6 h). Intraperitoneal administration of non-PEGylated spiegelmer CHF-F-037 (group b, 2000 nmol/kg) likewise produced an increased urine volume during the first two time periods. The water consumption of the animals in the period 0-6 h correlated to a large extent with the diuretic effect; in other words, in this period the rats drank more water the greater the measured volume of urine was, as shown in FIG. 16. With regard to the parameters urine volume and water consumption, there were no longer any significant differences between the individual groups in the following 6-24 h period.

Osmolality and Na Content of the Urine

The osmolality as well as the Na content of the urine is significantly lowered in a dose-dependent manner in the animals that had received active PEGylated spiegelmer i.v. and active non-PEGylated spiegelmer i.p., compared to the animals of the control groups, as is shown in FIGS. 18 and 19. Here a difference compared to the control animals can still be seen in the 6-24 h period at the highest dose in the case of the PEGylated spiegelmer after i.v. administration as well as in the non-PEGylated spiegelmer after i.p. administration. The decrease in the osmolality and Na content is evidence of the specific action of the spiegelmers. The inhibition of the AVP-$V_2$ receptor interaction leads to a decrease in the water resorption in the collecting tubules of the kidneys. As a result of this more water is excreted. Since however electrolytes are no longer excreted, the urine is significantly more dilute in a dose-dependent manner after treatment with the active spiegelmer. The AVP-binding spiegelmers therefore act, exactly like the $V_2$ receptor antagonists, not as a diuretic but as an aquaretic.

The features of the invention disclosed in the preceding description and in the claims and drawings may be essential both individually as well as in any arbitrary combination for the implementation of the invention in its various embodiments.

The invention claimed is:

1. An L-nucleic acid that binds a vasopressin comprising the formula:

5'-WWWWWWW-[Box2]-[Helix2]- --- -[Helix1]-[Box1]-3' in which --- denotes a polyethylene glycol (PEG) group in the 5'→3' direction between Helix1 and Helix2,
Helix1 and Helix2, in each case, comprises 6 or 7 nucleotides,
Helix1 and Helix2 are complementary and form a double-stranded helix,
WWWWWWW-Box2-Helix2 comprise SEQ ID NO: 54, wherein Box2 is the sequence GGGGUAGGGMUUG-GAHGGGHA (SEQ ID NO:50), in which M in each case and independently is A or C, and H in each case and independently is A, C or U, the W stretch WWWW-WWW consists of 0 to 7 Ws, in which W is A or U; and Helix1 and Box1 comprise the sequence NNNNNNNGUGGW (SEQ ID NO: 55), wherein Box1 is GUGGW, in which W is A or U, and W consist of 0 to 2 Ws.

2. The L-nucleic acid according to claim 1, wherein the PEG group has a molecular weight of about 172-688 Da.

3. The L-nucleic acid according to claim 1, with a sequence which is any one of SEQ ID NOS:38 & 62, 39 & 63, 40 & 63, 41 & 63, 42 & 63, 43 & 63, 43 & 44, 45 & 63, 45 & 46, 64 & 47, 64 & 48, 49 & 47, and 49 & 48, wherein the first identifier of each pair is 5'-WWWWWWW-[Box2]-[Helix2]

of the formula and the second identifier of each pair is

[Helix1]-[Box1]-3' of the formula.

4. The L-nucleic acid according to claim 1, wherein the vasopressin is human vasopressin.

5. The L-nucleic acid according to claim 1, wherein the vasopressin comprises an amino acid sequence according to SEQ ID NO:1.

6. The L-nucleic acid according to claim 1, wherein the L-nucleic acid comprises a further modification.

7. The L-nucleic acid according to claim 6, wherein the further modification comprises a PEG.

8. The L-nucleic acid according to claim 7, wherein the PEG comprises a straight-chain or a branched PEG.

9. A pharmaceutical composition comprising the L-nucleic acid according to claim 1 and a pharmaceutically acceptable carrier.

10. The L-nucleic acid according to claim 1, wherein W of the sequence NNNNNNNGUGGW is U.

11. The L-nucleic acid according to claim 1, wherein H is U.

12. The L-nucleic acid according to claim 1, wherein each of said Helix1 and Helix2 is 7 nucleotides.

13. The L-nucleic acid according to claim 1, wherein Helix1 and Helix2 each is 6 nucleotides.

14. The L-nucleic acid according to claim 1, wherein the W stretch is 0 Ws.

15. The L-nucleic acid according to claim 2, wherein the PEG group is about 344 Da.

16. The L-nucleic acid according to claim 7, wherein said PEG is about 20-120 kDa.

17. The L-nucleic acid according to claim 16, wherein said PEG is about 30-80 kDA.

18. The L-nucleic acid according to claim 17, wherein said PEG is about 40 kDA.

* * * * *